(12) United States Patent
Burkeen et al.

(10) Patent No.: US 12,305,156 B2
(45) Date of Patent: May 20, 2025

(54) SYSTEMS, DEVICES, AND METHODS FOR FLUID CONTROL IN A CELL PROCESSING SYSTEM

(71) Applicant: Cellares Corporation, South San Francisco, CA (US)

(72) Inventors: Lily Elizabeth Burkeen, San Francisco, CA (US); Kelly F. Curran, San Francisco, CA (US); Wilson Wai Toy, San Francisco, CA (US); Matthias Weber, South San Francisco, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 18/810,388

(22) Filed: Aug. 20, 2024

(65) Prior Publication Data
US 2025/0066708 A1 Feb. 27, 2025

Related U.S. Application Data

(60) Provisional application No. 63/520,859, filed on Aug. 21, 2023.

(51) Int. Cl.
*C12M 1/34* (2006.01)
*C12M 1/00* (2006.01)
*C12M 3/00* (2006.01)

(52) U.S. Cl.
CPC ............ *C12M 41/36* (2013.01); *C12M 23/40* (2013.01); *C12M 23/42* (2013.01); *C12M 23/58* (2013.01); *C12M 29/06* (2013.01); *C12M 41/34* (2013.01)

(58) Field of Classification Search
CPC ...... C12M 41/36; C12M 41/34; C12M 23/40; C12M 23/42; C12M 23/58; C12M 29/06
See application file for complete search history.

(56) References Cited

U.S. PATENT DOCUMENTS

| | | | |
|---|---|---|---|
| 3,728,227 A | 4/1973 | Elson et al. | |
| 4,234,023 A | 11/1980 | Sogi et al. | |
| 4,696,902 A | 9/1987 | Bisconte | |

(Continued)

FOREIGN PATENT DOCUMENTS

| | | |
|---|---|---|
| CN | 104203333 A | 12/2014 |
| CN | 108660060 A | 10/2018 |

(Continued)

OTHER PUBLICATIONS

ChargePoint (2021). Aseptic split butterfly valve 10-6 sterility assurance, located at https://www.thechargepoint.com/products/aseptic-split-butterfly-valve-10-6-sterility-assurance/, 2 total pages.

(Continued)

*Primary Examiner* — Michael L Hobbs
(74) *Attorney, Agent, or Firm* — Cooley LLP

(57) ABSTRACT

The present disclosure relates to systems, devices, and methods for automated fluid control within a cell processing system. In an embodiment, the present disclosure relates to a cartridge having a fluidic manifold comprising a first end panel, a second end panel, and a central panel connecting the first and second end panels, where each of the first and second end panels comprises a plurality of fluidic pathways model therein and a plurality of valves for controlling fluid flow through the plurality of fluidic pathways.

17 Claims, 20 Drawing Sheets

(56) References Cited

U.S. PATENT DOCUMENTS

| | | |
|---|---|---|
| 4,839,292 A | 6/1989 | Cremonese |
| 4,911,833 A | 3/1990 | Schoendorfer et al. |
| 5,058,619 A | 10/1991 | Zheng |
| 5,656,491 A | 8/1997 | Cassani et al. |
| 6,649,419 B1 | 11/2003 | Anderson |
| 7,550,287 B2 | 6/2009 | Hibino et al. |
| 7,745,209 B2 | 6/2010 | Martin et al. |
| 7,816,128 B2 | 10/2010 | Nakashima et al. |
| 8,158,426 B2 | 4/2012 | Wilson et al. |
| 8,158,427 B2 | 4/2012 | Wilson et al. |
| 8,168,432 B2 | 5/2012 | Wilson et al. |
| 8,273,572 B2 | 9/2012 | Martin et al. |
| 8,415,144 B2 | 4/2013 | Wilson et al. |
| 8,440,458 B2 | 5/2013 | Zijlstra et al. |
| 8,470,589 B2 | 6/2013 | Martin et al. |
| 8,492,140 B2 | 7/2013 | Smith et al. |
| 8,546,142 B2 | 10/2013 | Martin et al. |
| 8,697,443 B2 | 4/2014 | Wilson et al. |
| 8,727,132 B2 | 5/2014 | Miltenyi et al. |
| 8,809,044 B2 | 8/2014 | Wilson |
| 8,846,399 B2 | 9/2014 | Martin et al. |
| 8,956,860 B2 | 2/2015 | Vera et al. |
| 9,040,290 B2 | 5/2015 | Martin et al. |
| 9,045,721 B2 | 6/2015 | Martin et al. |
| 9,080,149 B2 | 7/2015 | Bosio et al. |
| 9,255,243 B2 | 2/2016 | Wilson et al. |
| 9,279,099 B2 | 3/2016 | Okano et al. |
| 9,290,730 B2 | 3/2016 | Martin et al. |
| 9,410,114 B2 | 8/2016 | Wilson et al. |
| 9,441,192 B2 | 9/2016 | Wilson et al. |
| 9,499,780 B2 | 11/2016 | Smith et al. |
| 9,534,195 B2 | 1/2017 | Smith et al. |
| 9,556,485 B2 | 1/2017 | Lin et al. |
| 9,567,565 B2 | 2/2017 | Vera et al. |
| 9,597,355 B2 | 3/2017 | Magnant |
| 9,625,463 B2 | 4/2017 | Miltenyi et al. |
| 9,701,932 B2 | 7/2017 | Smith et al. |
| 9,732,317 B2 | 8/2017 | Wilson |
| 9,783,768 B2 | 10/2017 | Larcher et al. |
| 9,845,451 B2 | 12/2017 | Martin et al. |
| 10,047,342 B2 | 8/2018 | Eibl et al. |
| 10,053,663 B2 | 8/2018 | Kabaha et al. |
| 10,119,970 B2 | 11/2018 | Miltenyi et al. |
| 10,131,876 B2 | 11/2018 | Kaiser et al. |
| 10,253,316 B2 | 4/2019 | Masquelier et al. |
| 10,294,658 B2 | 5/2019 | Scannon et al. |
| 10,323,258 B2 | 6/2019 | Bernate et al. |
| 10,329,559 B1 | 6/2019 | Masquelier et al. |
| 10,385,307 B2 | 8/2019 | Rowley et al. |
| 10,421,959 B1 | 9/2019 | Masquelier et al. |
| 10,508,288 B1 | 12/2019 | Bernate et al. |
| 10,519,437 B1 | 12/2019 | Masquelier et al. |
| 10,533,156 B2 | 1/2020 | Vera et al. |
| 10,584,333 B1 | 3/2020 | Masquelier et al. |
| 10,584,334 B1 | 3/2020 | Masquelier et al. |
| 10,588,994 B2 | 3/2020 | Kawamura et al. |
| 10,620,212 B2 | 4/2020 | Miltenyi et al. |
| 10,689,669 B1 | 6/2020 | Feldman et al. |
| 10,705,090 B2 | 7/2020 | Miltenyi et al. |
| 10,705,091 B2 | 7/2020 | Miltenyi et al. |
| 10,723,986 B2 | 7/2020 | Smith et al. |
| 10,724,043 B2 | 7/2020 | Sixto et al. |
| 10,844,338 B1 | 11/2020 | Smith et al. |
| 11,161,111 B2 | 11/2021 | Kabaha et al. |
| 11,198,845 B2 | 12/2021 | Parietti et al. |
| 11,371,018 B2 | 6/2022 | Shi et al. |
| 11,376,587 B2 | 7/2022 | Thakkar et al. |
| 11,447,745 B2 | 9/2022 | Shi et al. |
| 11,701,654 B2 | 7/2023 | Azersky et al. |
| 11,786,896 B2 | 10/2023 | Thakkar et al. |
| 11,826,756 B2 | 11/2023 | Azersky et al. |
| 11,872,557 B2 | 1/2024 | Biz et al. |
| 12,157,119 B2 | 12/2024 | Gerlinghaus et al. |
| 2003/0030272 A1 | 2/2003 | Johnson et al. |
| 2005/0070018 A1 | 3/2005 | Johnson et al. |
| 2005/0186671 A1 | 8/2005 | Cannon et al. |
| 2006/0194193 A1 | 8/2006 | Tsuruta et al. |
| 2006/0257999 A1 | 11/2006 | Chang et al. |
| 2007/0185472 A1 | 8/2007 | Baumfalk et al. |
| 2008/0057568 A1 | 3/2008 | Kan et al. |
| 2008/0176318 A1 | 7/2008 | Wilson et al. |
| 2009/0042281 A1 | 2/2009 | Chang et al. |
| 2009/0247417 A1 | 10/2009 | Haas et al. |
| 2010/0130732 A1 | 5/2010 | Chung et al. |
| 2010/0151571 A1 | 6/2010 | Vukasinovic et al. |
| 2011/0003380 A1 | 1/2011 | Miltenyi et al. |
| 2011/0229927 A1 | 9/2011 | Larsen et al. |
| 2012/0138156 A1 | 6/2012 | Hofman et al. |
| 2013/0115617 A1 | 5/2013 | Wilson |
| 2014/0309795 A1 | 10/2014 | Norton et al. |
| 2015/0307829 A1 | 10/2015 | Dedry et al. |
| 2016/0208216 A1 | 7/2016 | Vera et al. |
| 2016/0303563 A1 | 10/2016 | Granier et al. |
| 2016/0320381 A1 | 11/2016 | Holmes et al. |
| 2016/0320422 A1 | 11/2016 | Fritchie et al. |
| 2017/0058527 A1* | 3/2017 | Williams .................. E04D 1/34 |
| 2017/0307502 A1 | 10/2017 | Mason et al. |
| 2017/0313977 A1 | 11/2017 | Wilson |
| 2017/0321226 A1 | 11/2017 | Gill et al. |
| 2017/0348525 A1 | 12/2017 | Sano et al. |
| 2017/0362554 A1 | 12/2017 | Martin et al. |
| 2018/0031592 A1 | 2/2018 | Dority |
| 2018/0051243 A1 | 2/2018 | Hogan et al. |
| 2018/0078935 A1 | 3/2018 | Hung et al. |
| 2018/0185849 A1 | 7/2018 | Kaplan et al. |
| 2018/0196918 A1 | 7/2018 | Sadowski et al. |
| 2019/0212233 A1 | 7/2019 | Jovanovich et al. |
| 2019/0275519 A1 | 9/2019 | Castillo et al. |
| 2019/0292510 A1 | 9/2019 | Tandon et al. |
| 2019/0293673 A1 | 9/2019 | Wescott et al. |
| 2019/0316120 A1 | 10/2019 | Masquelier et al. |
| 2019/0330579 A1 | 10/2019 | Guenat et al. |
| 2020/0009557 A1 | 1/2020 | Frigard et al. |
| 2020/0025782 A1 | 1/2020 | Ahlfors |
| 2020/0048599 A1 | 2/2020 | Firouzi et al. |
| 2020/0095550 A1 | 3/2020 | Vera et al. |
| 2020/0159198 A1 | 5/2020 | Kapre et al. |
| 2020/0224147 A1 | 7/2020 | Rogers et al. |
| 2020/0292552 A1 | 9/2020 | Miltenyi et al. |
| 2020/0353004 A1 | 11/2020 | Nowak et al. |
| 2020/0368411 A1 | 11/2020 | Camisani et al. |
| 2020/0399578 A1 | 12/2020 | Corso et al. |
| 2020/0406221 A1 | 12/2020 | Dabrowski et al. |
| 2021/0001339 A1 | 1/2021 | Liu et al. |
| 2021/0032583 A1 | 2/2021 | Smith et al. |
| 2021/0047668 A1 | 2/2021 | Dabrowski et al. |
| 2021/0079344 A1 | 3/2021 | Bosio et al. |
| 2021/0147807 A1 | 5/2021 | Lickert et al. |
| 2021/0253997 A1 | 8/2021 | Wilson |
| 2021/0269755 A1 | 9/2021 | Smith et al. |
| 2021/0283565 A1 | 9/2021 | Gerlinghaus et al. |
| 2021/0283606 A1 | 9/2021 | Thakkar et al. |
| 2021/0301239 A1 | 9/2021 | Natsume et al. |
| 2021/0324318 A1 | 10/2021 | Parietti et al. |
| 2021/0354104 A1 | 11/2021 | Pesch et al. |
| 2022/0002652 A1 | 1/2022 | Patrick et al. |
| 2022/0047862 A1 | 2/2022 | Chang et al. |
| 2022/0143610 A1 | 5/2022 | Biz et al. |
| 2022/0150650 A1 | 5/2022 | Rucker |
| 2022/0325219 A1 | 10/2022 | Parietti et al. |
| 2022/0347683 A1 | 11/2022 | Thakkar et al. |
| 2023/0149922 A1 | 5/2023 | Thakkar et al. |
| 2023/0321650 A1 | 10/2023 | Azersky et al. |
| 2023/0415154 A1 | 12/2023 | Pesch et al. |
| 2023/0415155 A1 | 12/2023 | Biz et al. |
| 2024/0165613 A1 | 5/2024 | Azersky et al. |
| 2024/0254426 A1 | 8/2024 | Elpel et al. |
| 2024/0255537 A1 | 8/2024 | Malleo et al. |
| 2024/0279585 A1 | 8/2024 | Griffin et al. |
| 2024/0279588 A1 | 8/2024 | Malleo et al. |
| 2024/0318116 A1 | 9/2024 | Chang et al. |
| 2024/0326043 A1 | 10/2024 | Gerlinghaus et al. |
| 2024/0369586 A1 | 11/2024 | Tian et al. |
| 2024/0377420 A1 | 11/2024 | Cesarek |

(56) References Cited

U.S. PATENT DOCUMENTS

| | | | |
|---|---|---|---|
| 2024/0390897 | A1 | 11/2024 | Azersky et al. |
| 2024/0390898 | A1 | 11/2024 | Azersky et al. |
| 2024/0399365 | A1 | 12/2024 | Biz et al. |
| 2024/0402206 | A1 | 12/2024 | Boppart et al. |

FOREIGN PATENT DOCUMENTS

| | | | |
|---|---|---|---|
| EP | 0246912 | A2 | 11/1987 |
| EP | 0991389 | A1 | 4/2000 |
| EP | 0824380 | B1 | 1/2002 |
| EP | 3134512 | B1 | 1/2019 |
| EP | 2809449 | B1 | 10/2019 |
| EP | 3359294 | B1 | 5/2020 |
| EP | 3928867 | A1 | 12/2021 |
| GB | 2268187 | A | 1/1994 |
| JP | 2007325586 | A | 12/2007 |
| KR | 20130018286 | A | 2/2013 |
| WO | WO-2006102416 | A2 | 9/2006 |
| WO | WO-2006112870 | A1 | 10/2006 |
| WO | WO-2006118282 | A1 | 11/2006 |
| WO | WO-2007139742 | A1 | 12/2007 |
| WO | WO-2009072003 | A2 | 6/2009 |
| WO | WO-2017041051 | A1 | 3/2017 |
| WO | WO-2017123663 | A1 | 7/2017 |
| WO | WO-2018015561 | A1 | 1/2018 |
| WO | WO-2018102471 | A1 | 6/2018 |
| WO | WO-2020009700 | A1 | 1/2020 |
| WO | WO-2020014264 | A1 | 1/2020 |
| WO | WO-2021168368 | A1 | 8/2021 |
| WO | WO-2021183687 | A2 | 9/2021 |
| WO | WO-2021212124 | A1 | 10/2021 |
| WO | WO-2024112702 | A1 | 5/2024 |
| WO | WO-2024197093 | A2 | 9/2024 |
| WO | WO-2024206703 | A1 | 10/2024 |

OTHER PUBLICATIONS

CPC (2014). "6 traits of non-spill: How quick disconnect couplings evolved for low-pressure fluid handling," White Paper 8004, 4 total pages.
CPC (2014). "How single-use connections advance aseptic processing: Increased process flexibility and reliability, reduced costs," White Paper 7004, 6 total pages.
CPC (2018). Comparison Guide: Tube Welders and Aseptic Connectors, Technical Guide 7009, 3 total pages.
EMD Millipore (2015). "Lynx® S2S Connector—Low temperature compatibility (-80"C)," 4 total pages.
Final Office Action for U.S. Appl. No. 17/331,554 mailed Aug. 29, 2024, 18 pages.
Final Office Action for U.S. Appl. No. 18/652,602 mailed Nov. 1, 2024, 29 pages.
Final Office Action mailed on Apr. 28, 2022, for U.S. Appl. No. 17/198,134, filed Mar. 10, 2021, 11 pages.
Final Office Action mailed on Apr. 28, 2022, for U.S. Appl. No. 17/331,554, filed May 26, 2021, 16 pages.
Final Office Action mailed on Jul. 31, 2023, for U.S. Appl. No. 17/331,554, filed May 26, 2021, 19 pages.
Final Office Action mailed on Mar. 31, 2023, for U.S. Appl. No. 17/579,478, filed Jan. 19, 2022, 8 pages.
Garcia et al., "Microfluidic Screening of Electric Fields for Electroporation" Sci Rep. (2016) Feb. 19; 6:21238. pages 1-11.
Genetic Engineering & Biotechnology News (2006). "Thermal welding for sterile connections," located at https://www.genengnews.com/magazine/47/thermal-welding-for-sterile-connections/, 5 total pages.
International Search Report and Written Opinion for International Application No. PCT/US2023/080593 dated Mar. 21, 2024, 12 pages.
International Search Report and Written Opinion for PCT Application No. PCT/IB2024/058105 mailed Dec. 16, 2024, 12 pages.
International Search Report and Written Opinion for PCT Application No. PCT/US2024/022079 mailed Sep. 12, 2024, 25 pages.
International Search Report mailed on Oct. 13, 2021, for PCT Application No. PCT/US2021/021773, filed on Mar. 10, 2021, 13 pages.
Invitation to Pay Additional Fees for International Application No. PCT/US2024/022079 dated Jul. 17, 2024, 19 pages.
Jain, S et al. (2011). "The complete automation of cell culture: improvements for high-throughput and high-content screening," J. Biomol. Screen 16:932-939.
Kato, R et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.
Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). INTACT™ Connectors, located at https://www.medinstill.com/intactconnectors.php, 1 total page.
Millipore® (2020). "Technical Brief- Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors, Mm_NF-C188801, 2 total pages.
Non-Final Office Action for U.S. Appl. No. 18/244,051 mailed Oct. 9, 2024, 10 pages.
Non-Final Office Action for U.S. Appl. No. 18/652,602 mailed Jul. 17, 2024, 30 pages.
Non-Final Office Action for U.S. Appl. No. 18/759,602 mailed Nov. 8, 2024, 10 pages.
Non-Final Office Action for U.S. Appl. No. 18/792,358 mailed on Nov. 6, 2024, 5 pages.
Non-Final Office Action for U.S. Appl. No. 18/799,963 mailed Sep. 30, 2024, 9 pages.
Non-Final Office Action for U.S. Appl. No. 18/810,386 mailed Nov. 18, 2024, 8 pages.
Non-Final Office Action mailed on Apr. 24, 2024, for U.S. Appl. No. 17/331,554, filed May 26, 2021, 17 pages.
Non-Final Office Action mailed on Dec. 22, 2022, for U.S. Appl. No. 17/579,478, filed Jan. 19, 2022, 8 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed on Mar. 10, 2021, 5 pages.
Non-Final Office Action mailed on Jun. 26, 2023, for U.S. Appl. No. 17/198,134, filed Mar. 10, 2021, 15 pages.
Non-Final Office Action mailed on Mar. 16, 2023, for U.S. Appl. No. 17/331,554, filed May 26, 2021, 16 pages.
Non-Final Office Action mailed on May 14, 2024, for U.S. Appl. No. 18/611,632, filed Mar. 20, 2024, 13 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198,134, filed on Mar. 10, 2021, 7 pages.
Non-Final Office Action mailed on Sep. 13, 2023, for U.S. Appl. No. 18/141,329, filed Apr. 28, 2023, 7 pages.
Notice of Allowance (Corrected) mailed on Sep. 5, 2024, for U.S. Appl. No. 18/611,632, filed Mar. 20, 2024, 6 pages.
Notice of Allowance for U.S. Appl. No. 18/611,632 mailed Aug. 26, 2024, 9 pages.
Notice of Allowance for U.S. Appl. No. 18/811,490 mailed on Dec. 12, 2024, 8 pages.
Notice of Allowance mailed on Apr. 11, 2024, for U.S. Appl. No. 17/198,134, filed Mar. 10, 2021, 9 pages.

(56) References Cited

OTHER PUBLICATIONS

Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Mar. 22, 2023, for U.S. Appl. No. 17/992,784, filed Nov. 22, 2022, 8 pages.
Notice of Allowance mailed on Oct. 4, 2023, for U.S. Appl. No. 18/141,329, filed Apr. 28, 2023, 8 pages.
Pharma Japan, "Astellas Set to Cut Development Time with Cell Culture Robot, Eyes 4 Billion Yen Profit per Product" Aug. 9, 2023, 3 pages.
Qu, B et al., "Droplet Electroporation in Microfluidics for Efficient Cell Transformation with or without Cell Wall Removal," Lab Chip (2012) 12:4483-4488.
Saint Gobain (2017). "Pure-Fit® SC—Secure aseptic connections," Brochure, 5 total pages.
Sartorius Stedim Biotech (2011). "Opta® SFT," 4 total pages.
Schwartz C., "Optimizing Cell Separation with Beckman Coulter's Centrifugal Elutriation System," Beckmann Coulter Life Sciences (2014) 6 total pages.
SeriesLock™ (2021). Features and Specifications, located at https://serieslock.com/, 5 total pages.
Shi, Y et al. (1992). "Performance of Mammalian Cell Culture Bioreactor with a New Impeller Design," Biotechnology and Bioengineering 40:260-270.
STERIS (2018). "A compilation of material compatibilities with vaporized hydrogen peroxide," 2 total pages.
STERIS (2018). "Sterility assurance levels (SALS): Irradiation," 3 total pages.
STERIS (2020). "Overview of sterilization technology comparison," 1 total page.
Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.
U.S. Appl. No. 18/807,699, filed Aug. 16, 2024, by BEBAN et al.
U.S. Appl. No. 29/898,923, filed Aug. 2, 2024, by Gerlinghaus et al.
U.S. Appl. No. 18/759,602, filed Jun. 28, 2024, by Thakkar et al.
Written Opinion of the International Searching Authority mailed on Oct. 13, 2021, for PCT Application No. PCT/US2021/021773, filed on Mar. 10, 2021, 20 pages.

\* cited by examiner

1101

```
┌─────────────────────────────────────────────────────────────┐
│         Providing a fluid to a fluidic manifold of a cartridge   │
│                              1110                            │
└─────────────────────────────────────────────────────────────┘
                              ▼
┌─────────────────────────────────────────────────────────────┐
│  Flow the fluid through a fluidic pathway of one or more of a first end panel, a │
│        second end panel, and a central panel  1120           │
└─────────────────────────────────────────────────────────────┘
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│                  Perform a degassing process                 │
│                              1130                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│                   Perform a venting process                  │
│                              1140                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│   Measure one or more parameters via a window of the first end panel │
│                              1150                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│   Measure one or more parameters via a sensor of the central panel │
│                              1160                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│            Extract fluid via a fluid extraction port         │
│                              1170                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                              ▼
┌─────────────────────────────────────────────────────────────┐
│       Transfer fluid to another module of the cartridge  1180│
└─────────────────────────────────────────────────────────────┘
```

FIG. 11

SYSTEMS, DEVICES, AND METHODS FOR FLUID CONTROL IN A CELL PROCESSING SYSTEM

CROSS REFERENCE TO RELATED APPLICATIONS

This application claims priority to U.S. Provisional Patent Application Ser. No. 63/520,859 filed Aug. 21, 2023, the content of which is incorporated herein by reference in its entirety for all purposes.

TECHNICAL FIELD

The present disclosure relates to systems, devices, and methods for fluidic control in bioprocessing systems, and specifically, complex automated cell processing systems having multiple cell processing modules within a single cartridge.

BACKGROUND

Cell therapies involve collecting cells from an individual, processing the cells, and utilizing the processed cells to achieve a clinical response in the same or a different individual. Cell processing is a complex workflow that involves multiple steps, where each step typically requires a separate cell processing device and/or system to accomplish the specific step. Fluids, such as cellular material, may need to be transferred between different cell processing devices in order to achieve the final cell output. Improvements to cell processing systems have been made where multiple cell processing devices have been replaced by multiple modules within a single cartridge. However, even in these improved systems, fluids and cellular material must be transferred between the modules in order to perform distinct cell processing steps. Therefore, each module is typically fluidically connected to a fluid source by a fluid conduit. As more cell processing steps are included within a single cartridge or workflow, or as the desired throughput of cellular material increased, the number of modules typically grows proportionally. In turn, the quantity of fluid conduits connecting the required modules often becomes extremely complex. As the complexity of the fluidic pathways increases, entanglement of the fluid conduits becomes a significant issue during normal use and/or repair work in the event of any broken or damaged fluid conduits. Additionally, the complexity generally limits the total throughput as the fluid conduits may become inefficiently routed, which may increase the time required to transfer the required fluid to or from the associated module. The complexity may also limit the number of modules that may be included in the cell processing system, as the spatial requirements of the modules and/or fluid conduits can be significant. Accordingly, additional systems and methods for routing fluids in a cell processing system are desirable.

SUMMARY

The present disclosure relates generally to systems, devices, and methods for routing fluid flow within a bioprocessing system, such as an automated cell processing system. In general, a cartridge for cell processing may include a fluidic manifold comprising a first end panel, a second end panel, and a central panel connecting the first and second end panels. Each of the first and second end panels may include a plurality of fluidic pathways molded therein and a plurality of valves for controlling fluid flow through the plurality of fluidic pathways. In some variations, at least one of the plurality of valves may be a pinch valve.

The first end panel may further include at least one window configured for optical detection. In some variations, the at least one window may be a bubble sensing window. The first end panel may further include a bubble trap. The second end panel may further include at least one fluid extraction port. In some variations, the at least one fluid extraction port may be a needleless injection port. The first end panel may be fluidically connected to a first bioreactor module and the second end panel may be fluidically connected to a second bioreactor module.

The central panel may include a plurality of fluidic pathways. The plurality of fluidic pathways of the central panel may be fluidically connected to the plurality of fluidic pathways of each of the first and second end panels. The plurality of fluidic pathways of the central panel may be fluidically connected to one or more pumps. In some variations, the central panel may further include at least one pressure sensor configured to monitor fluid flow through the plurality of fluidic pathways of the central panel. The central panel may be coupled to a vent manifold configured to provide sterile air to the plurality of fluidic pathways of the central panel. The central panel may also be coupled to a degassing module, which may comprise an air permeable membrane. The central panel may connect to the first end panel and the second end panel via first and second bridges.

In some variations, the fluidic manifold may be fluidically connected to one or more modules of the cartridge. The one or more modules of the cartridge may be selected from the group consisting of an elutriation module, an electroporation module, a spinoculation module, and a cell sorting module.

Additional embodiments, features, and advantages of the invention will be apparent from the following detailed description and through practice of the invention.

BRIEF DESCRIPTION OF THE DRAWINGS

FIG. 11 is a flowchart of an illustrative variation of controlling fluid flow using a fluidic manifold.

DETAILED DESCRIPTION

Figure 1A:
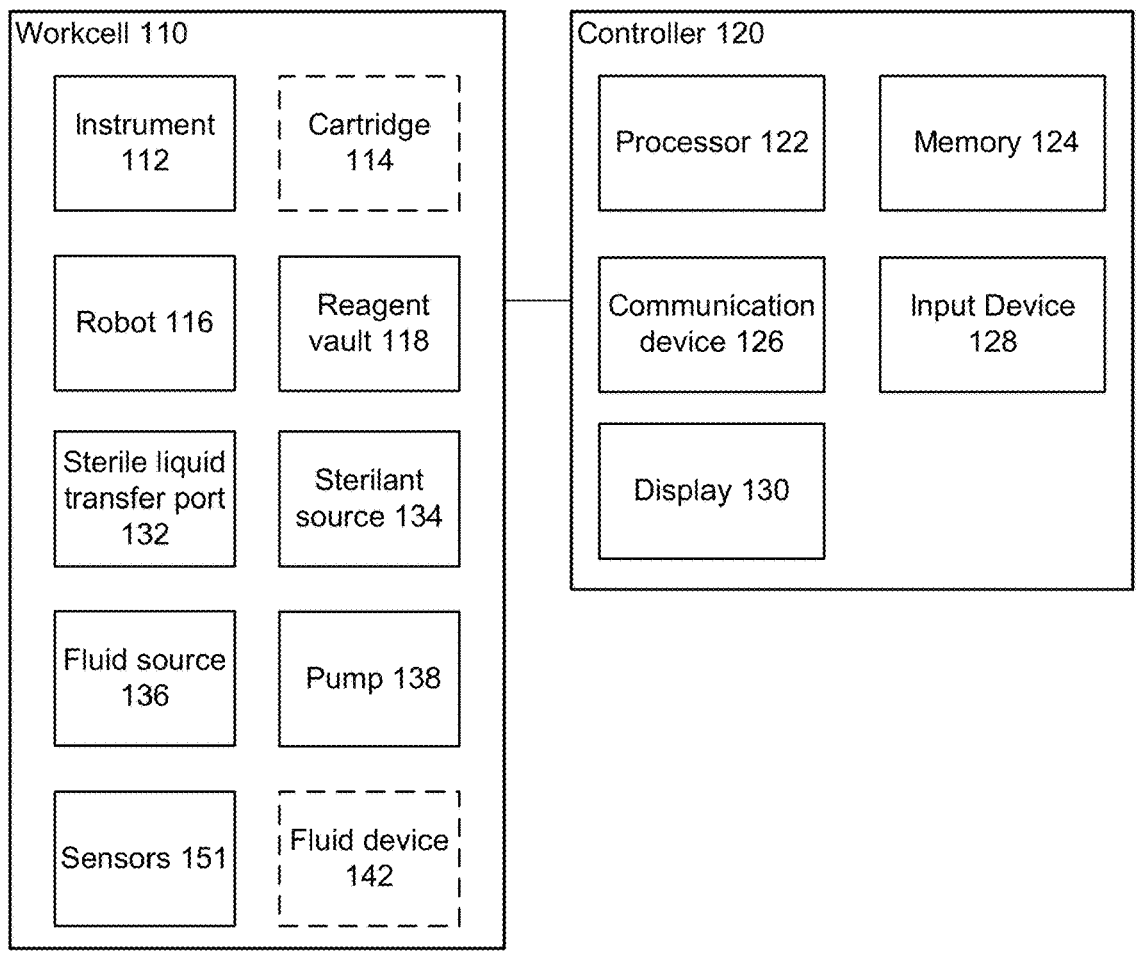
FIG. 1A is a block diagram of an illustrative variation of a cell processing system.

Disclosed herein are devices, systems, and methods for controlling fluid flow through and among cell processing modules of one or more cell processing cartridges to facilitate processing cells. Multiple cell processes, or cell processing steps, may be performed on cells within a cell processing system (e.g., workcell). The cell processing steps may each require one or more fluids (e.g., a cell suspension, a media, a buffer, a reagent). The one or more fluids may be provided to one or more modules of a cartridge of the workcell according to a pre-defined workflow. Accordingly, one or more fluids may flow through a fluidic manifold of the cartridge, such that the fluidic manifold may control the type, quantity, flow rate, timing, and/or destination of any fluid flowing therethrough. That is, the fluidic manifold may be connected to the one or more modules of the cartridge by one or more fluid conduits (e.g., tubes or channels). For example, the fluidic manifold may be fluidically connected to one or more of an elutriation module, an electroporation module, a spinoculation module, and a cell sorting module. The fluidic manifold may comprise one or more valves configured to control fluid flow through the one more fluid conduits. The fluidic manifold may also comprise one or more fluidic pathways. The fluidic manifold described herein may be configured to automatically control fluid flow through the cartridge.

The fluidic manifold may be optimized to reduce a quantity and/or a length of the fluid conduits coupled to the fluidic manifold. The optimization of the fluidic manifold may avoid entangling the fluid conduits. Entanglement may otherwise cause issues including delays in troubleshooting due to difficulties in identifying a specific fluid conduit and/or fluidic pathway. Furthermore, entanglement may cause a significant pressure drop in a fluid flowing through the one or more fluid conduits due to an unoptimized length and/or routing, which may require additional pumping capacity to provide the fluid to the destination at the desired flow rate. Accordingly, the optimization of the fluidic manifold described herein may enable an adjustable number of modules to be fluidically connected. In turn, the adjustable of the modules may facilitate a flexible workflow, such that the workflow may be modified to increase the total throughput of cellular byproducts for use in cell therapies. Accordingly, the fluid control system may be configured to automatically perform high-throughput cell processing in an automated cell processing system.

I. Cell Processing System

The cell processing systems described herein may be configured to perform one or more cell processing steps in a workcell. The workcell may comprise a closed, automated environment, which may be configured to maintain a sterile environment. The workcell may receive a cartridge and perform one or more cell processing steps on cells in a cell solution (e.g., cell suspension) contained within the cartridge. For example, the cell processing system may comprise a workcell comprising a plurality of instruments that may each be configured to independently perform one or more cell processing steps to the cells and/or cell solution, and a robot capable of moving the cartridge within the workcell (e.g., between one or more bays). The robot and/or instruments may be configured to automatically operate such that operator assistance may not be required at any point during the workflow. For example, the robot may receive the cartridge and move the cartridge between locations (e.g., instruments, bays, storage vaults, feedthroughs) within the workcell according to a pre-programmed workflow, where each location may be associated with one or more cell processing steps. After performing one or more cell processing steps of the pre-programmed workflow, the workcell may be configured to transfer the cartridge out of the workcell (e.g., via the robot). Additionally or alternatively, at least a portion of the cell solution may be transferred (e.g., via a fluid device or a fluidic manifold) to a second cartridge.

The cell solution (e.g., cell suspension) described herein may contain cells that may be processed for subsequent use in cell therapies. The cell solution may comprise cells (e.g., allogeneic cells) in a fluid, such as a media (e.g., cell culture media). The cell solution may contain cells from the same or different donors. Cells from the same donor may be split between one or more cartridges, such that separate cell processing steps may be performed on each of the cartridges and increase the overall throughput of the cell processing system described herein. The cell solution may be transferred to the cartridge prior to loading the cartridge into the workcell, such as by operating personnel. In some variations, the cartridge may be empty when loaded into the workcell such that the workcell may transfer a cell solution to the cartridge. In some variations, the cells from two or more cartridges may be combined according to a pre-determined ratio, which may correspond to an intended therapeutic treatment for a patient.

An illustrative cell processing system for use with the automated devices, systems, and methods is shown in FIG. 1A. Shown there is a block diagram of a cell processing system 100 comprising a workcell 110 and controller 120.

The workcell 110 may comprise one or more of an instrument 112, a robot 116 (e.g., robotic arm), a reagent vault 118, a sterile liquid transfer port 132, a sterilant source 129, a fluid source 136, a pump 138, and a sensor(s) 151. A cartridge 114 and a fluid device 142, which may be provided outside of the workcell 110 and used within the workcell 110, are illustrated in dashed lines. In some variations, the fluid device 142 may be a sterile liquid transfer device (SLTD). However, it should be appreciated that the fluid device 142 may be configured to transfer any fluid (which includes liquids), whether sterile or not. The controller 120 may comprise one or more of a processor 122, a memory 124, a communication device 126, an input device 128, and a display 130.

The workcell 110 may comprise a fully, or at least partially, enclosed housing inside which one or more cell processing steps may be performed in a fully, or at least partially, automated process. The cartridge 114 may be moved using the robot 116 to reduce manual labor in the cell processing steps, and fluid transfers into and out of the cartridge 114 may also be performed in a fully or partially automated process, as will be described in detail herein. For example, one or more fluids may be stored in a fluid device 142, such that the one or more fluids may be transferred to the cartridge 114 and/or removed from the cartridge 114 via the fluid device 142. In some variations, the fluid device 114 may be moved within the system 100 by the robot 116. Accordingly, the workcell 110 described herein advantageously enables the transfer of fluids in an automated and metered manner for automating cell therapy manufacturing.

The workcell 110 may facilitate fluid transfers and/or cartridge transfers. For example, in some variations, the robot 116 may be configured to move more than one cartridge 114 between different bays to perform a predetermined sequence of cell processing steps (e.g., workflow). In this way, multiple cartridges 114 may be processed in parallel, as different steps of the cell processing workflow may be performed at the same time on different cartridges. In another example, a sterile liquid transfer port 132 may be coupled between two or more cartridges 114 to transfer a cell product and/or other fluid between the cartridges 114. Furthermore, the sterile liquid transfer port 132 may be coupled between any set of fluid-carrying components of the system 100 (e.g., cartridge 114, reagent vault 118, fluid source 136, fluid device 142, etc.). For example, a first sterile liquid transfer port may be coupled between a first cartridge and a corresponding sterile liquid transfer port of a fluid device.

Other suitable cell processing systems and aspects thereof are provided in, e.g., U.S. patent application Ser. No. 17/198, 134, published as U.S. Patent Publication No. 2021/0283565, U.S. patent application Ser. No. 18/731,095, U.S. patent application Ser. No. 18/759,602, and U.S. patent application Ser. No. 18/807,699, the content of each of which is incorporated in its entirety by reference herein.

A. Cartridge

The cell processing systems described herein may comprise one or more cartridges having one or more modules configured to interface with, or releasably couple to, one or more instruments within the workcell. Some or all of the modules may be integrated in a fixed configuration within the cartridge, though they need not be. Indeed, one or more of the modules may be configurable or moveable within the cartridge, permitting various formats of cartridges to be assembled. For example, the cartridge may be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module may be defined by the set of connected components that collectively perform a predetermined function. However, the components of each module may or may not be physically grouped within the cartridge. In some embodiments, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments within the workcell interfaces with, or is releasably coupled to, its respective module or modules on the cartridge in order to carry out a specific cell processing step. For example, when a cartridge has an electroporation module, it may be moved by the robot to a bay within the workcell having an electroporation instrument within the workcell to perform electroporation on the cells within the cartridge. One advantage of such split module/instrument designs is that expensive components (e.g., motors, sensors, heaters, lasers, etc.) may be retained in the instruments of the system while less expensive components reside in the cartridge.

Figure 1B:
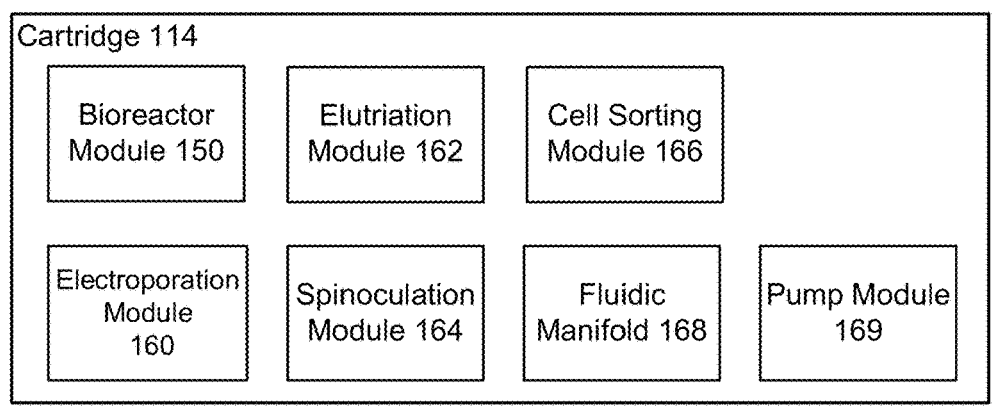
FIG. 1B is a block diagram of a cartridge that may be provided to the cell processing system of FIG. 1A.

As illustrated in FIG. 1B, the cartridge 114 may be configured to contain (e.g., house) a cell solution (e.g., cell suspension) for cell processing. Any number of cell processing steps may take place upon the cells within the cartridge. Accordingly, the cartridge 114 may comprise one or more of a bioreactor module 150, an electroporation module 160, an elutriation module 162, a spinoculation module 164, a cell sorting module 166, a fluidic manifold 168, and a pump module 169. The fluidic manifold 168 may be configured to transfer one or more fluids between one or more modules of the cartridge 114. For example, the fluidic manifold 168 may transfer a fluid from the pump module 169 to the bioreactor module 150. In another example, the fluidic manifold 168 may transfer a fluid (e.g., a cell solution) from the bioreactor module 150 to the cell sorting module 166. The cell solution may include cellular material, including target cells coupled to magnetic particles. In another example, the fluidic manifold 168 may transfer a fluid from the cell sorting module 166 to any other module 114, such as after a cell sorting process may have been performed. The fluidic manifold 168 may be configured to transfer the sorted cells (e.g., magnetically tagged cells) to one module and non-targeted cellular material to a different module.

The bioreactor module 150 may be configured to contain the cell solution. The bioreactor module 150 may further comprise a mixing chamber, in which the cell solution may be mixed with one or more reagents. The one or more reagents may comprise magnetic particles configured to couple to cells of a specific type (e.g., target cells). The elutriation module 162 may be configured to perform an elutriation process, wherein cellular material may be separated according to size, shape, and/or density. The spinoculation module 164 may be configured to perform a spinoculation process, wherein cells of different types may be bound together.

Other suitable cartridges and cell processing modules that may be used with the automatic cell processing work cells described herein are provided in, e.g., U.S. patent application Ser. No. 18/652,602, U.S. patent application Ser. No. 18/532,621, U.S. patent application Ser. No. 18/620,826, and U.S. patent application Ser. No. 18/611,632, the content of each of which is incorporated in its entirety by reference herein.

Figure 2B:
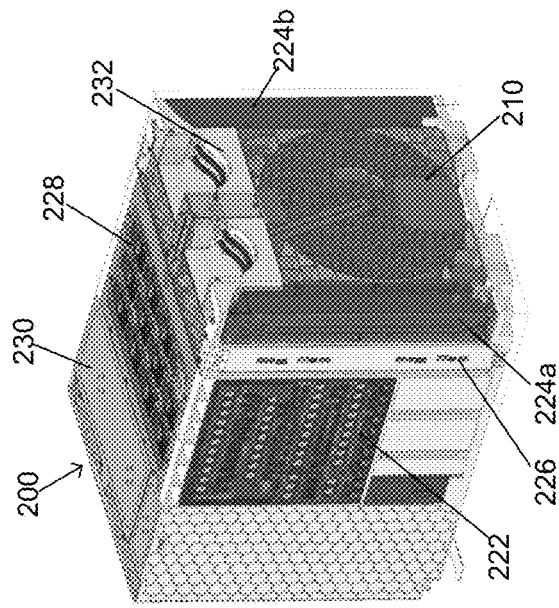
FIG. 2B is a rear perspective view of the cartridge shown in FIG. 2A.
Figure 2C:
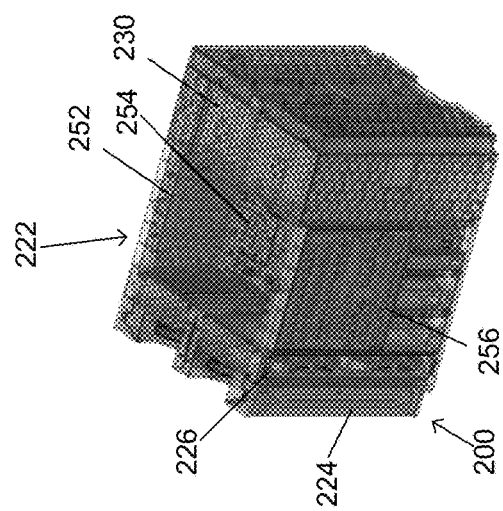
FIG. 2C is a front perspective view of another illustrative variation of a cartridge.
Figure 2A:
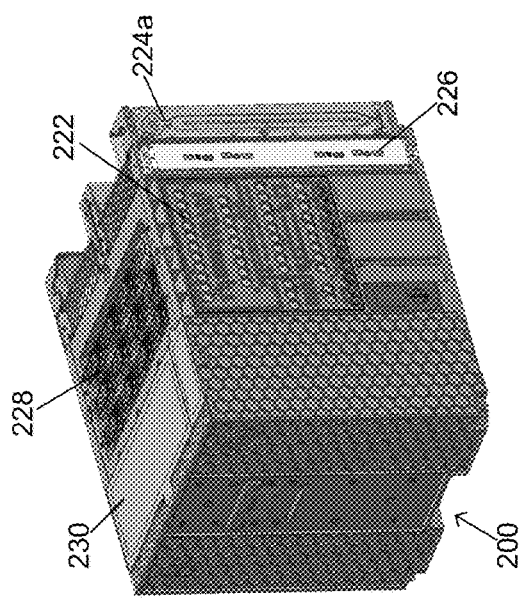
FIG. 2A is a front perspective view of an illustrative variation of a cartridge that may be provided to a cell processing system.

Referring to FIGS. 2A and 2B, an illustrative variation of a cartridge 200 is shown. The cartridge 200 may comprise an elutriation module 210, a fluidic manifold 222, a first cell sorting module 224a, a second cell sorting module 224b, an auxiliary module 226, a fluid device tray 228, a liquid container 230, and a pump module 232. While shown in these figures as having two cell sorting modules, it should be understood that any number of cell sorting modules may be used as desirable. For example, the cartridge may contain 1, 2, 3, 4, or even more cell sorting modules depending on the size of the cartridge, the existence of other cell processing modules within the cartridge, and so on. The cell sorting modules 224a, 224b may perform a magnetic cell sorting process. The electroporation module 220 may be configured to facilitate intracellular delivery of macromolecules (i.e., transfection by electroporation). An electrical discharge from one or more capacitors, or current sources, may generate sufficient current in the chamber to promote transfer of a polynucleotide, protein, nucleoprotein complex, or other macromolecule into the cells in the cell product. The fluidic manifold 222 may comprise at least one fluid conduit. The at least one fluid conduit of the fluidic manifold 222 may be configured to allow fluid to pass therethrough. For example, the at least one fluid may be a liquid or a gas. In some variations, the at least one fluid may comprise a solution of cells of varying sizes and densities. The fluidic manifold 222 may comprise at least one fluid inlet and at least one fluid outlet, and may comprise at least one valve. The fluidic manifold 222 may be fluidically connected to at least one module within the cartridge 200. For example, the fluidic manifold 222 may be configured to transfer at least one fluid to the first and/or second cell sorting modules 224a, 224b. The fluidic manifold 222 may be in communication with a controller, such as the controller 120 described in reference to FIG. 1A. For example, at least one valve of the fluidic manifold 222 may open and/or close in response to a command sent by the controller 120 to transfer fluid between various modules of the cartridge in accordance with a pre-determined workflow.

The fluid transfer port tray 228 may comprise one or more ports configured to transfer fluid to or from one or more fluid devices. That is, each port of the fluid transfer port tray 228 may be configured to facilitate a sterile liquid transfer. In some variations, each port may be fluidically connected to a fluid conduit configured to fluidically connect with at least one module of the cartridge 114. For example, each port of the fluid transfer port tray 228 may be fluidically connected to the fluidic manifold 222. In this way, a fluid may flow from a fluid device coupled to a port of the fluid transfer port tray 228 to the fluidic manifold 222, or vice versa. In some variations, each port of the fluid transfer port tray 228 may be fluidically connected to the liquid storage container 230. The liquid storage container 230 may be configured to contain a fluid. In some variations, the fluid may be a liquid or a gas. In some variations, the liquid storage container 230 comprises a plurality of liquid containers. For example, the liquid storage container 230 may comprise one container, two containers, or three containers. The liquid storage container 230 may be fluidically connected to at least one module of the cartridge 200. In some variations, the liquid container 230 may be fluidically connected to the fluidic manifold 222. Accordingly, a fluid may flow between a port of the fluid transfer port tray 228, the fluidic manifold 222, and the liquid storage container 230.

The cartridge may further comprise a pump module 232 having a pump configured to pump fluid in one or more directions along at least one fluid path. For example, the pump module 232 may be configured to pump a fluid to or from one or more of the elutriation module 210, the fluidic manifold 222, the cell sorting modules 224a, 224b, the auxiliary module 226, the fluid device tray 228, the liquid container 230, and any other module within the cartridge. The auxiliary module 226 may be configured to engage with at least one instrument and/or module. The auxiliary module 226 may comprise at least one electrical connector and/or at least one fluidic connector. In some variations, the auxiliary module 226 may be removed and replaced by any other module.

FIG. 2C shows an illustration variation of the cartridge 200 with the fluid device tray 228 removed. As shown, the fluidic manifold 222 may comprise a first end panel 252, a central panel 254, and a second end panel 256. The first end panel 252 and second end panel 256 may each define an external surface of the cartridge 200. The central panel 254 may be positioned within the cartridge 200, such that the central panel 254 may not define an external surface of the cartridge 200. The central panel 254 may extend between the first and second end panels 252, 256. That is, the central panel 254 may be coupled to each of the first and second end panels 252, 256. Accordingly, one or more fluidic pathways extend between the first and second end panels 252, 256 via the central panel 254. One or more of the first end panel, second end panel, and central panel may be fluidically connected to one or more of the other modules of the cartridge 200, including one or more of the elutriation module 210, the cell sorting modules 224a, 224b, the auxiliary module 226, the fluid device tray 228 (in reference to FIGS. 2A and 2B), and the liquid container 230.

Various materials may be used to construct the cartridge (including the modules thereof) and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings). The commercially available components may be attached or integrated with custom components or devices. The housing of the cartridge may constitute an additional layer of enclosure that further protects the sterility of the cell product.

i. Fluidic Manifold

In order for fluid to move between the various modules of the cartridge, the cartridges described herein comprise a novel fluidic manifold. The fluidic manifold may be configured to deliver a fluid (e.g., cell product(s)) to one or more modules according to a pre-defined workflow, which may be pre-programmed into a controller of a workcell as described herein throughout. The fluidic manifold can advantageously replace some or all tubing within the cartridge. The fluidic manifold may be controlled to deliver fluid to the cartridge modules in a pre-defined sequence according to a workflow, or may bypass one or more modules altogether using one or more valves. The fluidic manifold may be fluidically coupled to multiple fluid devices used to provide solutions or reagents, store cell products, or to collect waste solutions or reagents. The fluid may be a liquid or a gas. In some variations, the fluid may be a solution (e.g., a cell solution, a cell suspension). For example, the solution may comprise one or more of a cell, a media, a buffer, and a reagent.

The cartridge may comprise one or more pumps (e.g., of a pump module) fluidically connected to the fluidic manifold. The pump may be a direct lift pump, displacement pump, gravity pump, reciprocating pump, rotary pump, or peristaltic pump. In some embodiments, one or more of the instruments of the system may have one or more integrated pump actuators. This may permit the system to convey fluid between modules, fluidic containers, or other components while the cartridge may be interfaced to that module. The system (e.g., workcell) may also comprise a dedicated pump instrument configured to interface with a pump module comprising a pump.

The fluidic manifold may be used to facilitate a cell processing step. For example, in some variations, an enrichment step may comprise enriching a selected population of cells in a solution by conveying the solution to the elutriation module of the cartridge via the fluidic manifold, operating the robot to move the cartridge to an elutriation instrument so that the elutriation instrument may interface with the elutriation module, and operating the elutriation instrument to cause the elutriation module to enrich the selected population of cells.

In some variations, a washing step may comprise washing a selected population of cells in the solution by conveying the solution to the elutriation module of the cartridge via the fluidic manifold, operating the robot to move the cartridge to the elutriation instrument so that the elutriation module may interface with the elutriation instrument, and operating the elutriation instrument to cause the elutriation module to remove media from the solution, introduce media into the solution, and/or replace media in the solution. The removal and/or introduction of media may be performed by the fluidic manifold. During the enrichment step target cells may be enriched. Different enrichment steps may include, but are not limited to, platelet depletion, cytokine depletion, red blood cell depletion, and volume concentration.

In some variations, a selection step may comprise selecting a selected population of cells (e.g., by cell surface proteins) in the solution by conveying the solution to a selection module of the cartridge via the fluidic manifold, operating the robot to move the cartridge to a selection instrument so that the selection module interfaces with the selection instrument, and operating the selection instrument to cause the selection module to select the selected population of cells.

In some variations, a sorting step may comprise sorting a population of cells in the solution by conveying the solution to a sorting module of the cartridge via the fluidic manifold, operating the robot to move the cartridge to a sorting instrument so that the sorting module may interface with the sorting instrument, and operating the sorting instrument to cause the sorting module to sort the population of cells.

In some variations, a static step may be configured to maintain a fluid in an unagitated state. For example, the unagitated state may be associated with maintaining a fluid in a fluid device without stirring the fluid, such as with an impeller. In contrast, an agitated state may be associated with stirring the fluid via the impeller. In another example, the static step may comprise conveying the solution to a bioreactor module of the cartridge via the fluidic manifold, operating the robot to move the cartridge to the bioreactor instrument so that the bioreactor module may interface with the bioreactor instrument, and operating the bioreactor instrument to cause the bioreactor module to maintain the cells.

In some variations, an expansion step may comprise expanding the cells in the solution by conveying the solution to the bioreactor module of the cartridge via the fluidic manifold, operating the robot to move the cartridge to the bioreactor instrument so that the bioreactor instrument interfaces with the bioreactor module, and operating the bioreactor instrument to cause the bioreactor module to allow the cells to expand by cellular replication. The bioreactor instrument may provide closed-loop control of one or more of temperature, dissolved oxygen concentration, acidity (pH), and mixing intensity for the bioreactor. A single bioreactor instrument may interface with one or more bioreactors (e.g., multiple bioreactors of the same size or different size), or the system may comprise multiple bioreactor instruments. The bioreactor instrument may be designed to interface with several cartridges simultaneously.

In some variations, a tissue-digestion step comprises conveying an enzyme reagent via the fluidic manifold to a module containing a solution containing a tissue such that the enzyme reagent may cause digestion of the tissue to release a select cell population into the solution.

In some variations, an activating step, such as a T-cell activation step or an NK-cell activation step, may comprise activating a selected population of cells in the solution by conveying an activating reagent via the fluidic manifold to a module containing the solution containing cells.

In some variations, a transduction step comprises transducing a selected population of cells in the solution by conveying an effective amount of a vector, via the fluidic manifold, to a module containing the solution containing cells. Multiple vectors may be used in a single transduction step. The vector may be delivered with one or more proteins (e.g., a protein delivered in a liposome or a lipid nanoparticle) or using a cell penetrating peptide. The transduction step may comprise modifying cells by inserting, deleting, or mutating one or more polynucleotides in the cell (e.g., the genome of the cell, or any other polynucleotide in the cell).

In some variations, the fluidic manifold may be used more than once in a method of cell processing. In an illustrative method, the method may comprise culturing the cell product in a first bioreactor module; transferring the cell product to the elutriation module via the fluidic manifold to enrich for a desired cell type; transferring the cell product to a second bioreactor module via the fluidic manifold for a second culturing step; washing the elutriation module using a wash solution using fluid transferred by the fluidic manifold; and transferring the cell product to the elutriation module for a second enrichment step via the fluidic manifold.

Figure 1C:
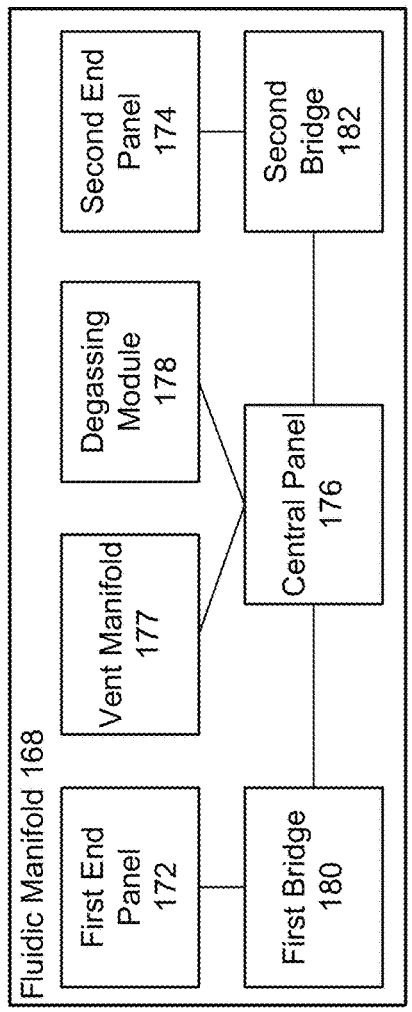
FIG. 1C is a block diagram of a fluidic manifold of the cartridge of FIG. 1B.

Referring to FIG. 1C, a block diagram of an exemplary variation of the fluidic manifold 168 is shown. The fluidic manifold 168 may comprise a first end panel 172, a second end panel 174, a first bridge 180, a second bridge 182, a central panel 176, a vent manifold 177, and a degassing module 178. The first and second end panels 172, 174 may be coupled to the central panel by the first and second bridges 180, 182. That is, the first end panel 172 may be coupled to the first bridge 180, which may also be coupled to the central panel 176. Similarly, the second end panel 174 may be coupled to the second bridge 182, which may also be coupled to the central panel 176. The end panels 172, 174 may be coupled to the respective bridges 180, 182 by a mechanical fastener (e.g., screws, nails, bolts), an adhesive (e.g., glue), a friction fit (e.g., a protrusion of one component received within a corresponding opening of another component, such as a fluid conduit), or a combination thereof.

One or more components of the fluidic manifold may be fluidically connected. For example, the first end panel 172 may be fluidically connected to the central panel 176 via the first bridge 180. That is, the first end panel 172 may comprise a fluidic pathway that is fluidically connected to a fluidic pathway of the first bridge 180, which, in turn, may be fluidically connected to a fluidic pathway of the central panel 176. Similarly, the second end panel 174 may be fluidically connected to the central panel 176 via the second bridge 182. That is, the second end panel 174 may comprise a fluidic pathway that is fluidically connected to a fluidic pathway of the second bridge 182, which, in turn, may be fluidically connected to a fluidic pathway of the central panel 176. In some variations, the first end panel 172 may be directly fluidically connected to the central panel 176, such that a fluidic connection therebetween may bypass the first bridge 180. Additionally, or alternatively, the second end panel 174 may be directly fluidically connected to the central panel 176, such that a fluidic connection therebetween may bypass the second bridge 182. The central panel 176 may be fluidically connected to one or more of the vent manifold 177 and degassing module 178. For example, a fluidic pathway of vent manifold 177 may be fluidically connected to a fluidic pathway of the central panel 176. Additionally, or alternatively, a fluidic pathway of degassing module 178 may be fluidically connected to a fluidic pathway of the central panel 176. In some variations, a fluidic pathway of the first and/or second end panel 172, 174 may be fluidically connected to the vent manifold 177 and/or degassing module 178.

Figure 1D:
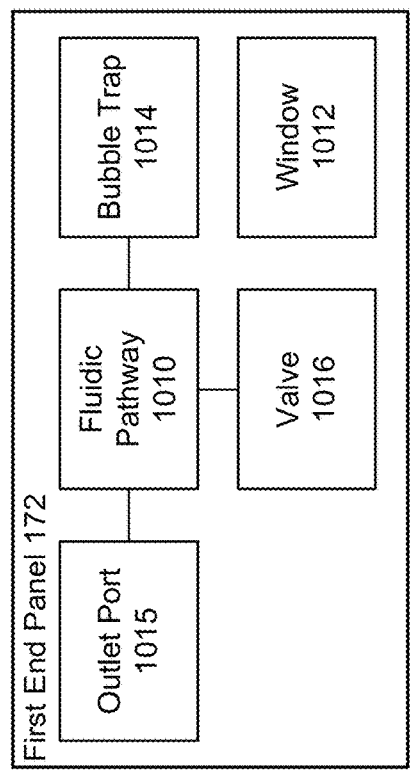
FIG. 1D is a block diagram of a first end panel of the fluidic manifold shown in FIG. 1C.

FIG. 1D shows a block diagram of an exemplary variation of a first end panel 172. The first end panel 172 may comprise a fluidic pathway 1010, a window 1012, a bubble trap 1014, an outlet port 1015, and a valve 1016. The fluidic pathway 1010 may be configured for fluid flow. In some variations, the first end panel 172 may comprise a plurality of fluidic pathways. The fluidic pathway 1010 may be defined by a groove, a depression, or a channel. In some variations, there may be between 1 and 70 fluidic pathways, 5 and 65 fluidic pathways, 10 and 60 fluidic pathways, or 15 and 55 fluidic pathways, including any value or sub-range therein. For example, in some variations, there may be 1, 5, 10, 15, 20, 25, 30, 35, 40, 45, 50, 55, or 60 fluidic pathways.

The fluidic pathway 1010 may be configured to facilitate one or more measurements. For example, the fluidic pathway 1010 may be covered by a film. The film may be transparent, such that one or more measurements of a fluid flowing through the fluidic pathway 1010 may be generated. The film may be removable, such that a user can remove the film to clean and/or repair the fluidic pathway 1010. In some variations, the film may be transparent, such that fluid within the fluidic pathway 1010 can be observed while maintaining a fluid-tight seal between the fluid within the fluidic pathway 1010 and an external environment. In some variations, the film may be integrally formed with the fluidic pathway, such that the film is not removable. Accordingly, the first end panel 172 may be manufactured from any biocompatible material that can facilitate the fluidic pathways described herein. For example, the first end panel 172, including the fluidic pathway 1010, may be molded, such as by compression, rotational, blow, and/or injection molding. In some variations, the fluidic pathway 1010 may be machined, extruded, or 3D printed. The fluidic pathway 1010 may be integrally formed with the first end panel or, in some variations, may be coupled thereto. In some variations, the first end panel 172 may be manufactured from a metal (e.g., aluminum), a polymer (e.g., polyethylene terephthalate glycol, polymethyl methacrylate), or a combination thereof. The film may be manufactured from a polymer (e.g., polyethylene terephthalate glycol, polymethyl methacrylate). In further variations, the film and first end panel 172 may be integrally formed using the same material.

The fluidic pathway 1010 may be fluidically connected to one or more fluidic control features. For example, the fluidic pathway 1010 may be fluidically connected to the valve 1016, outlet port 1015, and/or bubble trap 1014. The valve 1016 may be configured to control fluid flow through the fluidic pathway 1010. For example, the valve 1016 may be configured to transfer fluid from a module to the central panel 176. The valve 1016 may be actuatable, such that the valve 1016 may transition between an open configuration and a closed configuration. The valve 1016 may transition between configurations in response to a manual input, such as a user manually opening or closing the valve 1016 (e.g., by applying a translational force). In a further variation, the valve 1016 may transition between configurations in response to an electrical signal, such as a signal sent by the controller, e.g., such as controller 120 in FIG. 1A. In some variations, there may be between 1 and 60 valves, 1 and 50 valves, 10 and 50 valves, 20 and 50 valves, or 40 and 50 valves including any value or sub-range therein. For example, in some variations, there may be 1, 10, 20, 30, 35, 40, 43, 45, or 50 valves. In variations with a plurality of valves, each valve may be individually actuatable. For example, in variations with more than one valve, one or more valves may be opened while the remaining valves remain close. Similarly, one or more valves may be closed while the remaining valves remain open. The valve 1016 may comprise a pinch valve, a check valve, a ball valve, a diaphragm valve, or a gate valve. For example, the valve 1016 may comprise a pinch valve. The pinch valve may comprise a button, a fluid conduit, a spring, and a rod, such that applying a force to the button (e.g., pressing the button with a translation force) may transition the pinch valve from a closed configuration to an open configuration, or vice versa. In some variations, the open configuration may correspond to the spring in an extended (e.g., undepressed) configuration, such that fluid may flow through the fluid conduit. The closed configuration may correspond to the spring in a retracted (e.g., depressed) configuration, such that the rod blocks the fluid conduit so fluid may not flow through the fluid conduit. In further variations, the configurations may be opposite, such that the open configuration corresponds to a retracted spring configuration and the closed configuration corresponds to an extended spring configuration. In still further variations, the pinch valve may comprise more than one fluid conduit. In such a variation, a first fluid conduit may be open and a second fluid conduit may be closed. The configuration of each fluid conduit may switch upon applying a force to the button.

The bubble trap 1014 may be configured to perform a bubble trapping process. A fluid, such as a fluid having a mixture of liquid and gas (e.g., bubbles), may flow through the bubble trap 1014 via the fluidic pathway 1010. The bubble trap 1014 may be configured to retain the gas while allowing the liquid to continue flowing out of the bubble trap 1014 via the fluidic pathway 1010. For example, the bubble trap 1014 may contain an amount of fluid (e.g., liquid and gas), such that any additional fluid that enters the bubble trap may interact with the fluid already within the bubble trap 1014. That is, any gas within the additional fluid may rise to a top surface of the liquid already within the bubble 1014, and any liquid within the additional fluid may mix with the liquid already within the bubble 1014. The gas may remain within the bubble trap 1014 and the liquid may flow out of the bubble trap 1014. In some variations, the bubble trap 1014 may comprise a gas permeable membrane (e.g., one-way gas permeable). That is, a fluid may flow into the bubble trap 1014 such that it contacts (e.g., impinges) the membrane so any gas within the fluid may permeate through the membrane while any liquid within the fluid may not permeate therethrough. The liquid may continue to flow out of the bubble trap 1014 while the gas may remain trapped by the membrane. Accordingly, the bubble trap 1014 may be configured to provide substantially bubble-free liquid to other portions of the fluidic manifold 168. The bubble trap 1014 may comprise a shape suitable to perform the bubble trapping process. For example, the bubble trap may be shaped as a triangle, a rectangle, a trapezoid, a circle, or combination thereof. Any number of bubble traps may be used as desirable. In some variations, there may be between 1 and 5 bubble traps, 1 and 4 bubble traps, or 1 and 3 bubble traps, including 1, 2, 3, 4, or 5 bubble traps.

The outlet port 1015 may be configured to transfer fluid to and/or from another component of the fluidic manifold. For example, the outlet port 1015 may be configured to transfer fluid from the first end panel 172 to the central panel 176. That is, fluid may flow from the valve 1016 through the outlet port 1015. In another example, the outlet port 1015 may be configured to receive fluid from the central panel 176. That is, fluid may flow through the outlet port 1015 to the valve 1016. The outlet port 1015 may be fluidically connected to a bridge connected to a central panel, such as the first bridge 180. That is, a sterile fluid transfer may occur between the outlet port 1015 and a corresponding fluid transfer port of the first bridge 180. In some variations, the first end panel may comprise a plurality of outlet ports. For example, in some variations, there may be between 1 and 60 outlet ports, 10 and 60 outlet ports, 20 and 60 outlet ports, or 40 and 60 outlet ports, or any value or sub-range therein. For example, in some variations, there may be 1, 5, 10, 20, 30, 40, 45, 50, 55, or 60 outlet ports. The number of outlet ports may correspond to a number of fluid transfer ports (e.g., end panel transfer ports) of a corresponding bridge.

The window 1012 may be configured to facilitate a measurement of the fluid. For example, the measurement may comprise a bubble count value. The bubble count value may represent the quantity of bubbles within the fluid. The bubble count value may be compared to a pre-defined condition (e.g., a threshold value). The comparison may be performed by the controller 120 and, in some variations, may determine a response by the fluidic manifold. For example, the response may comprise routing the fluid, via the fluidic pathway 1010, through the bubble trap 1014 if the comparison indicates that the bubble count value meets or exceeds the pre-defined condition. Accordingly, the window 1012 may be transparent. In some variations, the window 1012 may be manufactured using a material with a suitable translucence, such as a polymer (e.g., polyethylene terephthalate glycol, polymethyl methacrylate). Any number of windows may be used as desirable. In some variations, there may be between 1 and 60 windows, 10 and 60 windows, 20 and 60 windows, or 40 and 60 windows, or any value or sub-range therein. For example, in some variations, there may be 1, 5, 10, 20, 30, 40, 45, 50, 55, 57, or 60 windows.

Figure 1F:
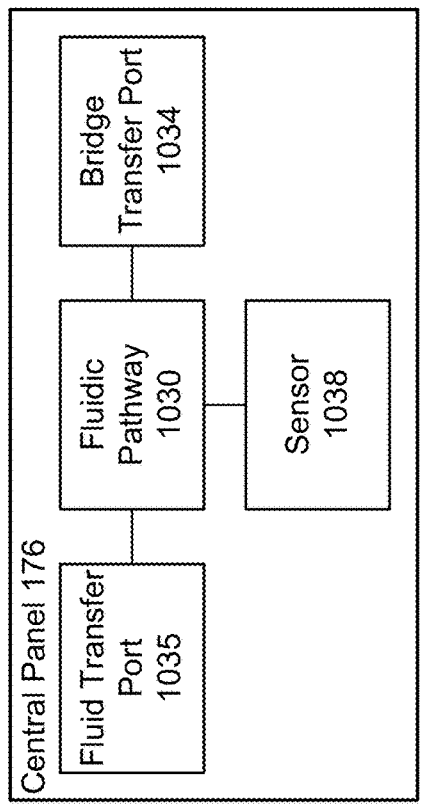
FIG. 1F is a block diagram of a central panel of the fluidic manifold shown in FIG. 1C.
Figure 1E:
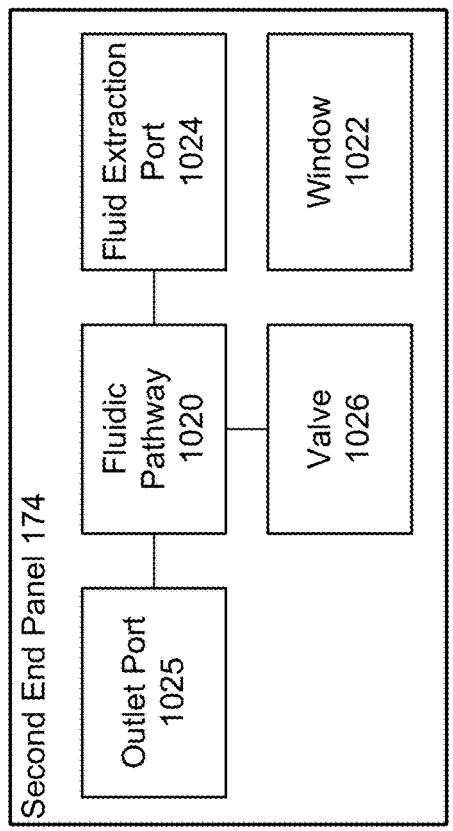
FIG. 1E is a block diagram of a second end panel of the fluidic manifold shown in FIG. 1C.

FIG. 1E shows a block diagram of an exemplary variation of a second end panel 174. The second end panel 174 may comprise a fluidic pathway 1020, a window 1022, a fluid extraction port 1024, an outlet port 1025, and a valve 1026. The fluidic pathway 1020, window 1022, outlet port 1025, and valve 1026 may correspond to the descriptions provided for the fluidic pathway 1010, window 1012, outlet port 1015, and valve 1016 in reference to FIG. 1D. The fluid extraction port 1024 may be configured to transfer fluid out of the second end panel. That is, fluid from any location of the fluidic manifold may be flowed to the fluid extraction port of the second end panel 174. Accordingly, the fluid extraction port 1024 may be used to extract at least a portion of the fluid within the fluidic manifold 168. The fluid extraction port 1024 may advantageously provide an extraction path that may be used to quickly remove fluid from the fluidic manifold 168, such as in an emergency. An emergency may comprise a loss of electrical power, a leak elsewhere in the fluidic manifold, fluid stuck in one or more locations of the fluidic manifold and/or cartridge, or another workflow interruption. In some variations, the fluid extraction port 1024 may comprise a needless injection port. Accordingly, the fluid extraction port 1024 may form a liquid and/or gas impermeable barrier that may be pierced by a user (e.g., using a syringe) during a fluid extraction process, and subsequently reformed upon termination of the fluid extraction process. The fluid extraction process may include using a fluid conduit to couple to the fluid extraction port 1024, receiving fluid from the fluidic pathway associated with the fluid extraction port 1024, and subsequently decoupling from the fluid extraction port 1024. Any number of fluid extraction ports may be used as desirable. In some variations, there may be between 1 and 20 fluid extraction ports, 1 and 15 fluid extraction ports, or 5 and 15 fluid extraction ports, or any value or sub-range therein. For example, in some variations, there may be 1, 5, 8, 10, 11, 12, 15, or 20 fluid extraction ports.

FIG. 1F shows a block diagram of an exemplary variation of a central panel 176. The central panel 176 may comprise a fluidic pathway 1030, a fluid transfer port 1035, a bridge transfer port 1034, and a sensor 1038. The fluidic pathway 1030 may define a fluid flow path through the central panel 176. In some variations, the central panel 176 may comprise a plurality of fluidic pathways. The fluidic pathway 1030 may be defined by a groove, a depression, a channel, or the like. The fluidic pathway 1030 may comprise a cross-sectional shape suitable for transporting a fluid, such as a circle, a square, a triangle, a trapezoid, or a combination thereof. In some variations, the fluidic pathway 1030 may comprise a sidewall (e.g., of a circular cross-section) or more than one sidewall (e.g., of a rectangular cross-section). The fluidic pathway 1030 may be fluidically connected to one or more of the fluid transfer port 1035, bridge transfer port 1034, and sensor 1038. Any number of fluidic pathways may be used as desirable. In some variations, there are between 1 and 50 fluidic pathways, 10 and 50 fluidic pathways, 20 and 50 fluidic pathways, or 30 and 50 fluidic pathways, any value or sub-range therein. For example, in some variations, there may be 1, 5, 10, 15, 20, 25, 30, 35, 40, 45, or 50 fluidic pathways. The central panel 176 may be manufactured from any biocompatible material that can facilitate the fluid pathways described herein. For example, the central panel 176, including the fluidic pathway 1030, may be molded, such as by compression, rotational, blow, and/or injection molding. In some variations, the central panel 176, including the fluidic pathway 1030, may be machined, extruded, or 3D printed. The fluidic pathway 1030 may be integrally formed with the central panel 176 or, in some variations, may be coupled thereto. In some variations, the central panel 176 may be manufactured from a metal (e.g., aluminum), a polymer (e.g., polyethylene terephthalate glycol, polymethyl methacrylate), or a combination thereof.

The fluid transfer port 1035 may be configured to receive a fluid from one or more modules of a cartridge. That is, a fluid conduit (e.g., tube) may fluidically connect the one or more modules to the fluid transfer port 1035. The fluid transfer port 1035 may comprise a seal, such that a sterile fluid transfer may occur therethrough. Accordingly, fluid may flow from one or more modules to the fluidic pathway 1030, such that the fluid may be transferred to other components of the fluidic manifold 168. The bridge transfer port 1034 may be configured to receive fluid from a bridge, such as the first bridge 180 or the second bridge 182. For example, a fluidic pathway of the first bridge 180 may be fluidically connected to the bridge transfer port 1034. In some variations, a fluidic pathway of the second bridge 182 may be fluidically connected to the bridge transfer port 1034. The bridge transfer port 1036 may comprise a seal, such that a sterile fluid transfer may occur therethrough. Accordingly, fluid may flow from one or more bridges (and in some variations, one or more end panels) to the fluidic pathway 1030, such that the fluid may be transferred to other components of the fluidic manifold 168.

The sensor 1038 may be configured to measure one or more parameters of the fluid flowing through the central panel 176 (e.g., via the fluidic pathway 1030). In some variations, the sensor 1038 may comprise a pressure sensor (e.g., piezoelectric sensor, strain gauge sensor), an optical sensor (e.g., camera), a temperature sensor, or a humidity sensor. The one or more parameters may include a pressure value, a dissolved oxygen value, a pH value, or a cell count value. For example, the sensor 1038 may comprise a pressure sensor configured to measure a pressure value of the fluid. The pressure value may be between about 1 psi and about 25 psi, about 1 psi and about 20 psi, or about 1 psi and about 15 psi, including about 1 psi, about 5 psi, about 10 psi, about 15 psi, or about 25 psi. The pressure value may be useful in indicating the status of a fluid in an associated fluid channel. For example, a non-zero pressure value may indicate that fluid may be flowing through the associated fluid channel. In another example, a pressure value may be compared to an expected value to determine whether the expected fluid volume may be flowing through the associated fluid channel. A pressure value that doesn't align with the expected value may indicate that there may be an issue (e.g., clog, leak, bubbles) somewhere in the system that is reducing the flow rate. In some variations, the central panel may comprise a plurality of sensors. For example, in some variations, there may be between 1 and 20 sensors, 1 and 16 sensors, 6 and 14 sensors, or 8 and 12 sensors, including 1, 2, 4, 6, 8, 10, or 12 sensors. In some variations, a plurality of sensors may define an analytical instrument, such that a plurality of measured parameters may be generated and/or reviewed in tandem.

In some variations, the sensor 1038 may correspond to one or more pumps of the pump module 169 that may be fluidically connected to the central panel 176. In some variations, the central panel 176 may be fluidically connected to 1, 2, 3, 4, 5, 6, 7, 8, 9, or 10 pumps of the pump module 169. Accordingly, the sensor 1038 may be configured to monitor fluid flow from and/or to the central panel 176 via the one or more pumps. A flex circuit may be wired to the sensor 1038. The flex circuit may be coupled to the central panel 176. In some variations, the flex circuit may be located elsewhere in the fluidic manifold 168 or, in further variations, any other suitable location of the cartridge 114.

The flex circuit may be wired configured to communicate with the controller 120, such that a user may remotely monitor the measurements generated by the sensor 1038. In some variations, one or more of the sensor 1038 and flex circuit may be in wireless communication with the controller 120, which may reduce or eliminate the quantity of wires within the cartridge 114.

Figure 1G:
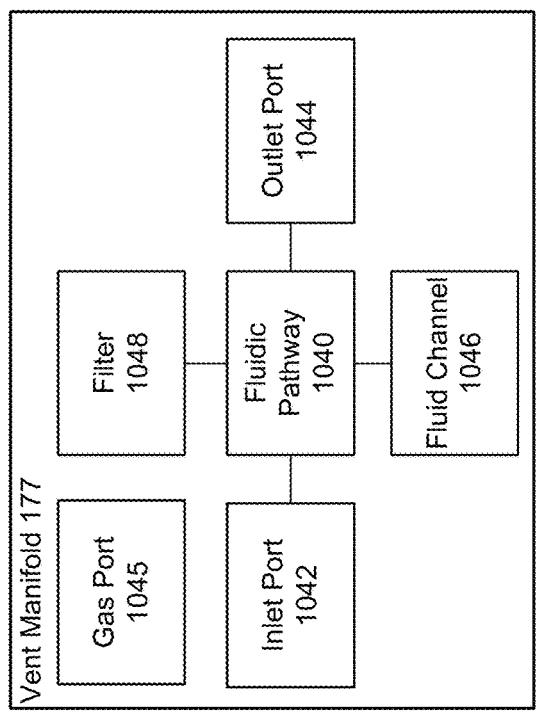
FIG. 1G is a block diagram of a vent manifold of the fluidic manifold shown in FIG. 1C.

FIG. 1G shows a block diagram of an exemplary variation of a vent manifold 177. The vent manifold 177 may comprise a fluidic pathway 1040, an inlet port 1042, an outlet port 1044, a gas port 1045, a fluid channel 1046 (e.g., fluid cavity), and a filter 1048. The inlet port 1042 and/or outlet port 1044 may be fluidically connected the fluidic pathway 1040. The inlet port 1042 and/or outlet port 1044 may be configured to receive a fluid. In some variations, the inlet port 1042, outlet port 1044, and/or gas port 1045 may be fluidically connected to the central panel 176 via a fluid conduit (e.g., a tube). For example, a first end of a first fluid conduit may be coupled to the inlet port 1042 and a second end of the fluid conduit may be coupled to the fluid transfer port 1035, such as a first fluid transfer port. In another example, a first end of a second fluid conduit may be coupled to the outlet port 1044 and a second end of the fluid conduit may be coupled to the fluid transfer port 1035, such as a second fluid transfer port. In yet another example, a first end of a third fluid conduit may be coupled to the gas port 1045 and a second end of the fluid conduit may be coupled to the fluid transfer port 1035, such as a third fluid transfer port. Accordingly, fluid may flow into the vent manifold 177 via the inlet port 1042 and out of the vent manifold 177 via the outlet port 1044. Before, during, and/or after fluid may flow through the inlet port 1042 and/or outlet port 1044, a gas may flow through the gas port 1045. Any number of inlet, gas, and/or outlet ports may be used as desirable, and there may be more inlet ports than outlet ports or vice versa. In some variations, there may be between 1 and 10 inlet ports, 1 and 8 inlet ports, or 1 and 3 inlet ports, including 1, 2, 3, 4, or 5 inlet ports. In some variations, there may be between 1 and 10 outlet ports, 1 and 8 outlet ports, or 1 and 3 outlet ports, including 1, 2, 3, 4, or 5 outlet ports. In some variations, there may be between 1 and 10 gas ports, 1 and 8 gas ports, or 1 and 3 gas ports, including 1, 2, 3, 4, or 5 gas ports.

The fluidic pathway 1040 may define a fluid flow path through the vent manifold 177. In some variations, the vent manifold 177 may comprise a plurality of fluidic pathways. The fluidic pathway 1040 may be defined by a groove, a depression, channel, or the like. The fluidic pathway 1040 may comprise a cross-sectional shape suitable for transporting a fluid, such as a circle, a square, a triangle, a trapezoid, or a combination thereof. In some variations, the fluidic pathway 1040 may comprise a sidewall (e.g., of a circular cross-section) or more than one sidewall (e.g., of a rectangular cross-section). In some variations, there may be between 1 and 10 fluidic pathways, 1 and 8 fluidic pathways, or 1 and 5 fluidic pathways, including 1, 2, 3, 4, or 5 fluidic pathways. The fluidic pathway 1040 may be fluidically connected to one or more of the inlet port 1042, outlet port 1044, gas port 1045, fluid channel 1046, and filter 1048. For example, a fluid may flow through the inlet port 1042, along the fluidic pathway 1040, through the filter 1048, and through the outlet port 1044. Accordingly, the filter 1048 may be configured to remove one or more particles (e.g., solid particles) from the fluid flowing along the fluidic pathway 1040. Additionally, or alternatively, a fluid may flow through the gas port 1045, along the fluidic pathway 1040, and into the fluid channel 1046. The vent manifold 177, including the fluidic pathway 1040 and/or any other component thereof, may be molded, such as by such as by compression, rotational, blow, and/or injection molding. The fluidic pathway 1040 may be integrally formed with the vent manifold 177 or, in some variations, may be coupled thereto. In some variations, the vent manifold 177 may be manufactured from a metal (e.g., aluminum), a polymer (e.g., polyethylene terephthalate glycol, polymethyl methacrylate), or a combination thereof.

The vent manifold 177 may be configured to perform a venting process. The venting process may be configured to mitigate effects associated with clogs and/or condensation. For example, the filter 1048 may remove a quantity of particles from the fluid flowing along the fluidic pathway 1040 that flow through the filter 1048 may become restricted. Restricted flow may correspond to a reduced flow rate, an increased pressure drop by the fluid, and/or an increased pressure of the fluid. In another example, a fluid may condense on one or more internal surfaces of the vent manifold 177 or the central panel, such as the fluidic pathways 1030, 1040. Without proper mitigation, the condensation may inhibit fluid flow through the vent manifold 177. Accordingly, the venting process may mitigate the effects of clogging and/or condensation by transferring a gas from an external environment into the fluidic pathway 1040 of the vent manifold 177 and/or transferring a gas from the fluidic pathway 1040 to the external environment. For example, the gas may be contained in the fluid channel 1046, such that the gas may be selectively released into the fluidic pathway 1040 to release any particles that may have clogged the filter 1048 and/or remove any condensed fluid within the fluidic pathway 1040. The fluid channel 1046 may comprise a volume corresponding to the volume of gas required to perform the venting process. For example, in some variations, the volume of the fluid channel 1046 may be between about 0.25 mL to about 5 mL, about 0.5 mL to about 2.5 mL, about 0.5 mL to about 1.5 mL, or about 0.75 mL to about 1.25 mL, including about 0.25 mL, about 0.5 mL, about 0.75 mL, about 1 mL, about 2 mL, or about 3 mL. In some variations, there may be a plurality of fluid channels, such as between 1 and 10 fluid channels, including 1, 2, 3, 4, 5, 6, 7, 8, 9, or 10 fluid channels. The fluid channels may be fluidically connected to each other or, in some variations, may not be. Each fluid channel may be configured to perform the venting process described herein.

Figure 1H:
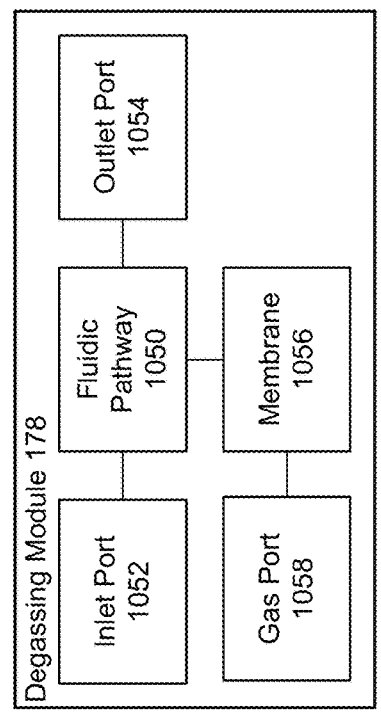
FIG. 1H is a block diagram of a degassing module of the fluidic manifold shown in FIG. 1C.

FIG. 1H shows a block diagram of an exemplary variation of a degassing module 178. The degassing module 178 may comprise a fluidic pathway 1050, an inlet port 1052, an outlet port 1054, a gas port 1058, and a membrane 1056. The inlet port 1052 and/or outlet port 1054 may be fluidically connected the fluidic pathway 1040. The inlet port 1052 and/or outlet port 1054 may be configured to receive a fluid. In some variations, the inlet port 1052 and/or outlet port 1054 may be fluidically connected to the central panel 176 via a fluid conduit (e.g., a tube). For example, a first end of a first fluid conduit may be coupled to the inlet port 1052 and a second end of the fluid conduit may be coupled to the fluid transfer port 1035, such as a first fluid transfer port. In another example, a first end of a second fluid conduit may be coupled to the outlet port 1054 and a second end of the fluid conduit may be coupled to the fluid transfer port 1035, such as a second fluid transfer port. Accordingly, fluid may flow into the degassing module 178 via the inlet port 1052 and out of the vent manifold 177 via the outlet port 1054. In some variations, there may be between 1 and 10 inlet ports, 1 and 8 inlet ports, or 1 and 3 inlet ports, including 1, 2, 3, 4, or 5 inlet ports. In some variations, there may be between 1 and 10 outlet ports, 1 and 8 outlet ports, or 1 and 3 outlet ports, including 1, 2, 3, 4, or 5 outlet ports.

The fluidic pathway 1050 may define a fluid flow path through the degassing module 178. In some variations, the degassing module 178 may comprise a plurality of fluidic pathways. For example, in some variations, there may be between 1 and 10 fluidic pathways, 1 and 5 fluidic pathways, or 1 and 3 fluidic pathways, including 1, 2, 3, 4, 5, or 10 fluidic pathways. The fluidic pathway 1050 may be defined by a groove, a depression, or a channel. The fluidic pathway 1050 may comprise a cross-sectional shape suitable for transporting a fluid, such as a circle, a square, a triangle, a trapezoid, or a combination thereof. In some variations, the fluidic pathway 1050 may comprise a sidewall (e.g., of a circular cross-section) or more than one sidewall (e.g., of a rectangular cross-section). The membrane 1056 may cover at least a portion of the fluidic pathway 1050, such that there may be a surface area of contact between the membrane and a fluid flowing through the fluidic pathway. The gas port 1058 may be positioned on an opposite side of the membrane 1056 relative to the fluidic pathway 1050. The membrane 1056 may be a gas permeable membrane. For example, the membrane 1056 may be configured to allow a gas (e.g., air) to permeate from the fluidic pathway 1050 to the gas port 1058, while retaining liquid within the fluidic pathway 1050. In some variations, the membrane may be manufactured from super hydrophobic polyvinylidene fluoride (PVDF), polyether sulfone (PES), polydimethylsiloxane (PDMS) or polytetrafluoroethylene (PTFE). The degassing module 178, including the fluidic pathway 1050 and/or any other component thereof, may be molded, such as by such as by compression, rotational, blow, and/or injection molding. The fluidic pathway 1050 may be integrally formed with the degassing module 178 or, in some variations, may be coupled thereto. In some variations, the degassing module 178 may be manufactured from a metal (e.g., aluminum), a polymer (e.g., polyethylene terephthalate glycol, polymethyl methacrylate), or a combination thereof.

The degassing module 178 may be configured to perform a degassing process. The degassing process may be configured to remove a gas from a liquid (e.g., a dissolved gas). For example, during the degassing process a suction (e.g., vacuum) may be applied to the gas port 1058, such that a gas (e.g., air) may be pulled out a fluid flowing along the fluidic pathway 1050 of the degassing module 178. In some variations, the fluidic pathway 1050 may define a tortuous fluid path configured to maximize a ratio of the contact surface area to the volume of the fluid. The tortuous path may include a plurality of bends in the fluidic pathway 1050. Maximizing the ratio of surface area contact to fluid volume may increase the efficacy of the degassing process by increasing the duration of exposure of the fluid to the suction as the fluid flows along the fluidic pathway 1050. The degassing module 178 may be used alone or in combination with the bubble trap 1014 described in reference to FIG. 1D.

The central panel 176 may be configured to selectively route fluid through one or more of the vent manifold 177 and the degassing module 178. That is, in some variations, the central panel 176 may route substantially all fluid through one or more of the vent manifold 177 and the degassing module 178. In further variations, the central panel 176 may not route at least a portion of the fluid through either of the vent manifold 177 and the degassing module 178. The determination to route the fluid through the vent manifold 177 and/or the degassing module 178 may correspond to a pre-determined workflow and/or the type of fluid. For example, a fluid comprising cells may not be routed through either of the vent manifold 177 or the degassing module 178 to avoid clogging the component(s), whereas a fluid comprising a media, a buffer, and/or a reagent may be routed through one or more of the vent manifold 177 and the degassing module 178.

Figure 3A:
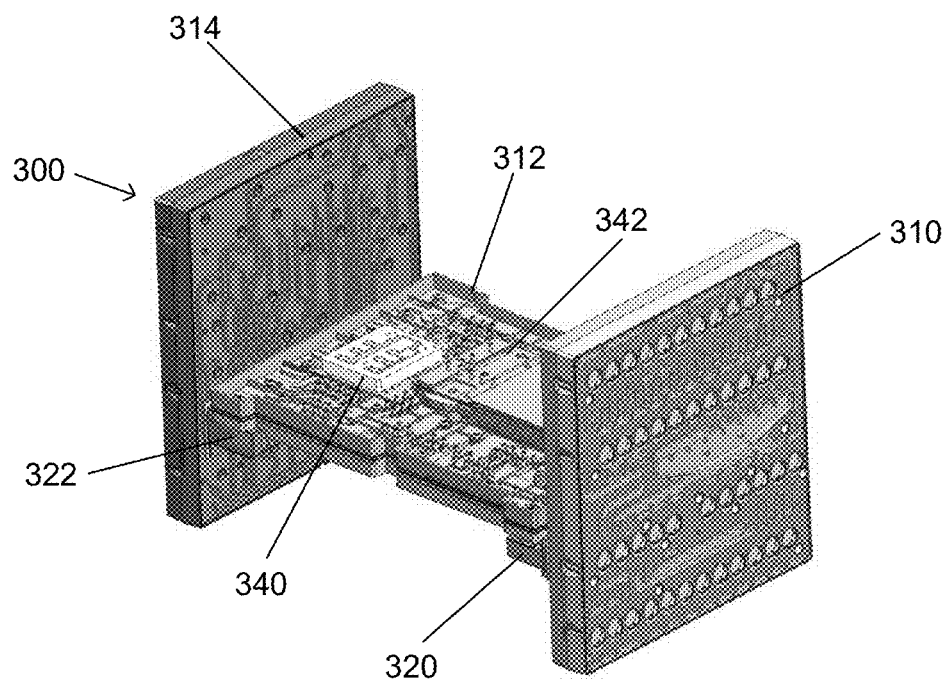
FIG. 3A is a front perspective view that shows a top side of an illustrative variation of a fluidic manifold of a cartridge.
Figure 3B:
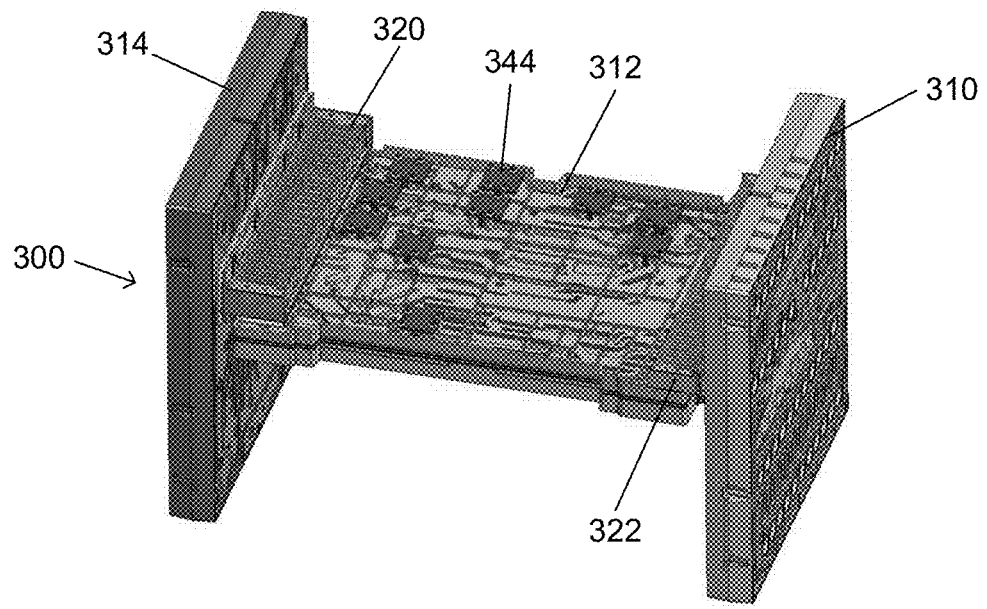
FIG. 3B is a rear perspective view that shows a bottom side of the fluidic manifold shown in FIG. 3A.
Figure 3C:
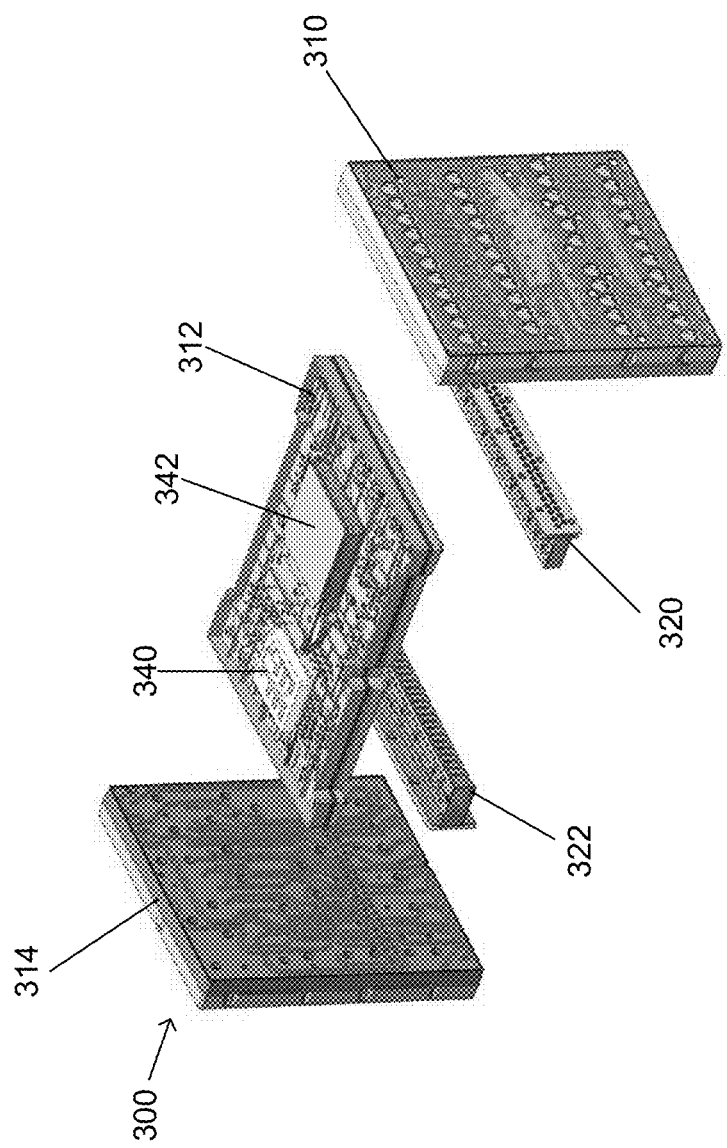
FIG. 3C shows an exploded view of the fluidic manifold shown in FIG. 3A.

FIGS. 3A-3C show an exemplary variation of a fluidic manifold 300. The fluidic manifold 300 may comprise a first end panel 310, a second end panel 314, a central panel 312, a first bridge 320, a second bridge 322, a degassing module 340 and a vent manifold 342. The first end panel 310 may be coupled to the first bridge 320. The first bridge 320 may be coupled to the first end panel 310 parallel to a lateral dimension of the first end panel 310. The first bridge 320 may be coupled to the first end panel 310 at a pre-determined position along the longitudinal dimension of the first end panel. For example, in some variations, the pre-determined position may be about ¼, about ⅓, about ½, or about % of the longitudinal dimension. The first bridge 320 may be coupled to the central panel 312 at a first end of the central panel 312. The first end panel 310 may be perpendicular to the central panel 312, such that the longitudinal dimension of the first end panel 310 may be perpendicular to a longitudinal dimension of the central panel 312. Accordingly, the pre-determined position of the first bridge 320 relative to the first end panel 310 may provide a volume on one or more sides of the central panel 312, such that one or more fluid transfer ports of the central panel 312 may be accessed by a user.

The second end panel 314 may be coupled to the second bridge 320. The second bridge 322 may be coupled to the central panel 312 at a second end of the central panel 312. The first end of the central panel 312 may be opposite the second end of the central panel 312. The second bridge 322 may be coupled to the second end panel 320 in a similar fashion as described for the first bridge 320 and first end panel 310. Accordingly, in some variations, at least a portion of the first and second bridges 320, 322 may be coplanar.

The central panel 312 may be further coupled to the degassing module 340 and vent manifold 342. For example, the degassing module 340 and vent manifold 342 may be coupled to a front surface of the central panel 312. The front surface of the central panel 312 may be opposite to a rear surface of the central panel 312. Coupled to the rear surface of the central panel 312 may be a sensor 344. In some variations, there may be a plurality of sensors coupled to the rear surface of the central panel 312. The sensor 344 may be configured to measure one or more parameters of a fluid flowing through the central panel 312. The couplings described herein may be facilitated by a mechanical fastener (e.g., screws, nails, bolts), an adhesive (e.g., glue), a friction fit (e.g., a protrusion of one component received within a corresponding opening of another component), or a combination thereof.

a. End Panel

The fluidic manifold described herein may comprise one or more end panels. The end panel may comprise one or more fluidic pathways. For example, the end panel may be configured to transfer fluid via the fluidic pathways to and/or from one or more modules of the cartridge. The end panels may be coupled to a central panel. The fluidic pathways of the end panel may be fluidically connected to one or more fluidic pathways of the central panel. In some variations, a plurality of end panels may be coupled to the central panel. For example, the end panels may be coupled to separate ends of the central panel. Accordingly, the quantity, size, and/or shape of the end panel(s) may correspond to the size and/or shape of the central panel. In some variations, the end panel may comprise a cross-sectional shape such as rectangular, a triangle, a square, a trapezoid, a circle, or a combination thereof. In some variations, there may be between 1 and 10 end panels, 1 and 6 end panels, or 1 and 4 end panels, including 1, 2, 3, 4, 5, or 6 end panels.

Figure 4B:
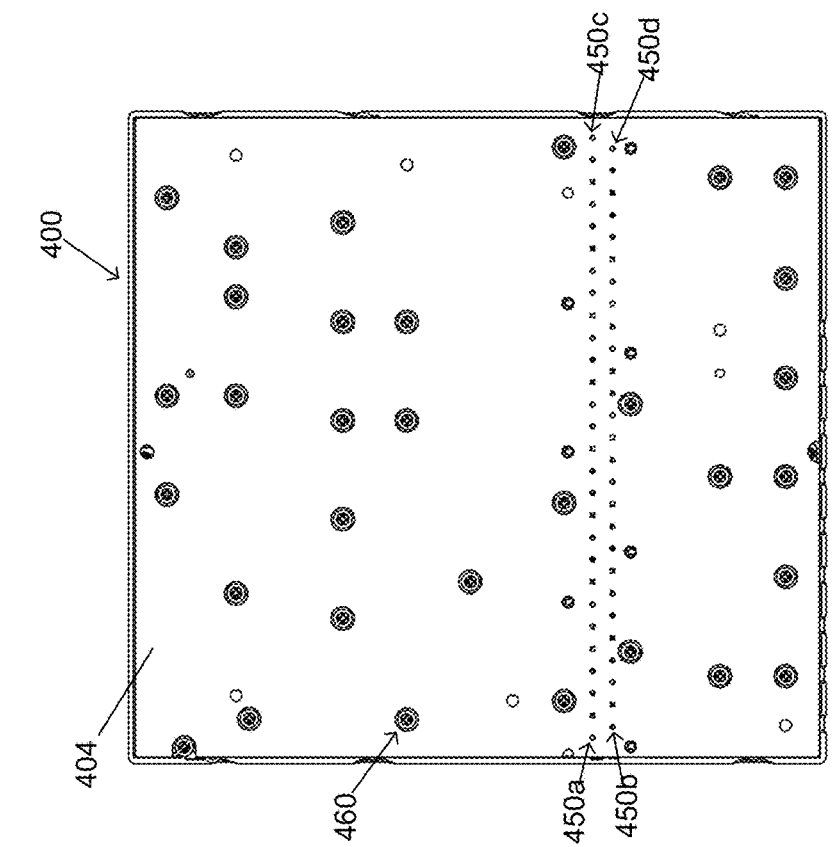
FIG. 4B shows a rear view of the first end panel shown in FIG. 4A.
Figure 4A:
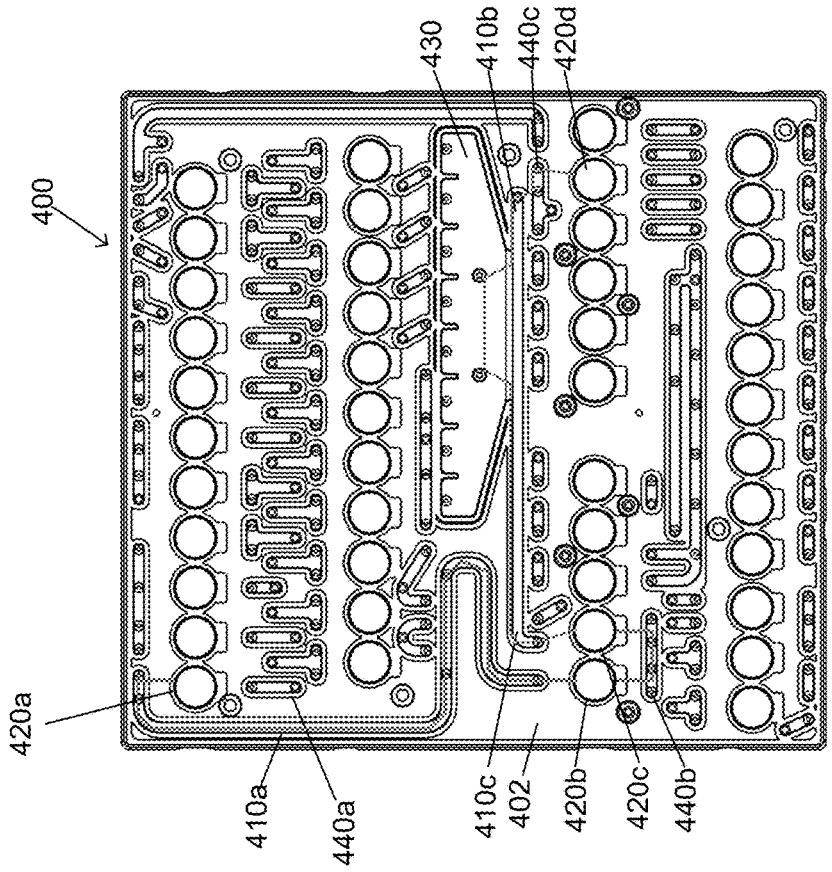
FIG. 4A shows a front view of an illustrative variation of a first end panel of a fluidic manifold.
Figure 4C:
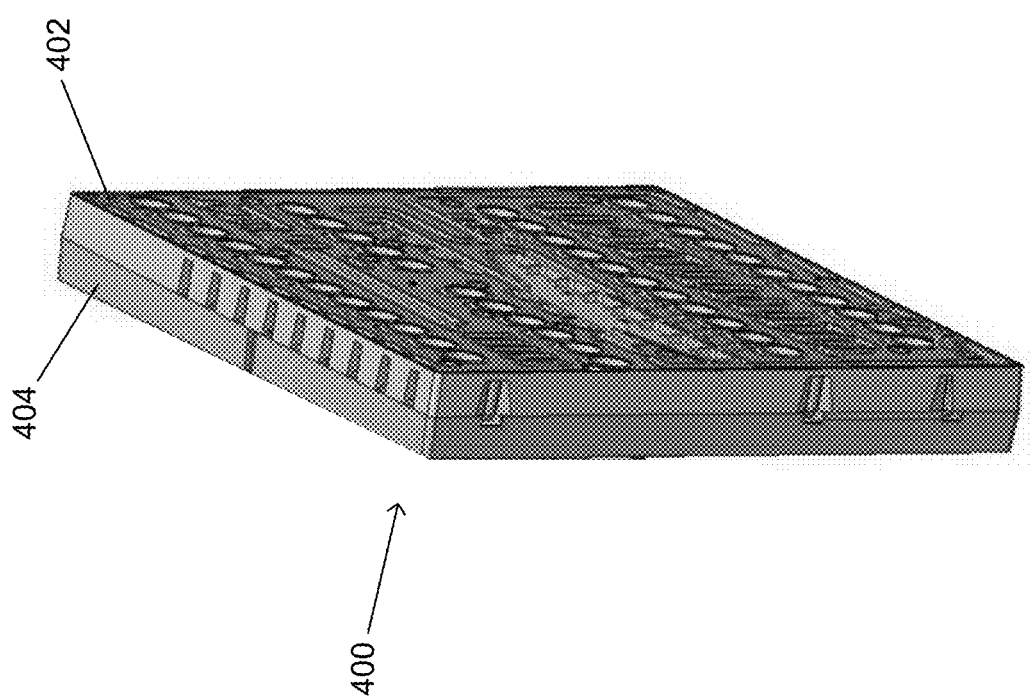
FIG. 4C shows a perspective view of the first end panel shown in FIG. 4A

FIGS. 4A-4C show a first end panel 400. The first end panel 400 may comprise a plurality of fluid pathways 410a-410c, a plurality of valves 420a-420d, a bubble trap 430, a plurality of windows 440a-440c, a plurality of outlet ports 450a-450d, and a fastener 460. FIG. 4A shows a first body 402 of a first end panel 400. The first body 402 of the first end panel 400 may define one or more fluid pathways, such as a first fluid pathway 410a, a second fluid pathway 410b, a third fluid pathway 410c, and so on. The fluid pathways of the first body 402 of the first end panel 400 may be covered by a film (not shown). The film may be configured to maintain a fluid-tight seal between a fluid flowing through the fluidic pathway(s) and the external environment. In some variations, the film may also cover the bubble trap 430. The windows 440a-440c may be configured to facilitate one or more measurements of a fluid. That is, the windows 440a-440c may correspond to one or more fluidic pathways, such that a sensor operatively coupled to the windows 440a-440c may generate a measurement of the fluid in the fluidic pathways. For example, the windows 440a-440c may be transparent, such that an optical measurement may be generated. The optical measurement may correspond to, for example, a bubble count value.

Fluid may flow through the fluidic pathways, valves, and windows of the first end panel 400 in a variety of routes. That is, the plurality of valves 420a-420d may be used to direct (e.g., control) the fluid according to a desired route. For example, as shown in FIG. 4A, the valve 420a may be fluidically connected to the fluidic pathway 410a. Accordingly, fluid may flow through the valve 420a to the fluidic pathway 410a when the valve 420a is in an open position. In some variations, the valve 420a may be actuated (e.g., via a controller) to a closed position, such that fluid may not flow to the fluidic pathway 410a. Fluid may flow along the fluidic pathway 410a to the valve 420b. Similarly, the position (e.g., open or closed) of the valve 420b may determine whether fluid may flow therethrough. The valve 420b may be fluidically connected to the window 440b. That is, fluid that does flow through the valve 420b may flow proximate to the window 440b. The window 440b may be fluidically connected to the valve 420c, such that the fluid may flow through the valve 420c if open or may not flow therethrough if the valve 420c is closed. If the valve 420c is open, the fluid may flow to the fluidic pathway 410c. The fluidic pathway 410c may be fluidically connected to the bubble trap 430. Accordingly, any bubbles within the fluid flowing along the fluidic pathway 410c may be removed as the fluid flows through the bubble trap 430. The fluid may exit the bubble trap 430 to continue flowing along the fluidic pathway 410c. The fluidic pathway 410c may be fluidically connected to the window 440c, such that any remaining bubbles of the fluid may be observed. Then, the window 440c may be fluidically connected to the valve 420d, such that the position of the valve 420d may determine whether fluid may flow therethrough. The valve 420d may be fluidically connected to an outlet port, such as the outlet port 450b. Accordingly, fluid may flow from the valve 420a to the outlet port 450b. Alternative routes may be achieved by the positions of any of the valves of the first end panel 400 according to one or more valve actuation inputs provided by the controller.

FIG. 4B shows a second body 404 of a first end panel 400. As shown, the plurality of outlet ports 450a-450d may extend along a lateral dimension of the second body 404 of the first end panel 400. That is, the plurality of outlet ports 450a-450d be arranged in a collinear arrangement along a line that extends from a first end of the first end panel 400 to a second end of the first end panel 400. In some variations, the plurality of outlet ports 450a-450d be arranged in one or more rows. For example, the outlet ports 450a and 450c may form a first row and the outlet ports 450b and 450d may form a second row. The plurality of outlets ports 450a-450d may be fluidically connected to one or more fluidic pathways of the first end panel 400. The plurality of outlet ports 450a-450d may be configured to transfer fluid from the one or more fluidic pathways to another component of the fluidic manifold. For example, the plurality of outlet ports 450a-450d may comprise a size, shape, and/or position that may correspond to a plurality of ports of a first bridge (not shown). In some variations, the second body 404 may comprise one or more fluidic pathways, which may correspond to the description provided for the fluidic pathways of the first body 402.

The two bodies 402, 404 of the first end panel 400 may be coupled together. For example, the first body 402 shown in FIGS. 4A and 4C and the second body 404 shown in FIGS. 4B and 4C may together form the first end panel 400. In some variations, the first and second bodies 402, 404 may be coupled together by a mechanical fastener (e.g., screws, nails, bolts), an adhesive (e.g., glue), a friction fit (e.g., a protrusion of one component received within a corresponding opening of another component), or a combination thereof. For example, the first and second bodies 402, 404 may be coupled together by the fastener 460. That is, the fastener 460 may extend through each of the first and second bodies 402, 404, such that the first and second bodies 402, 404 may be securely coupled. In some variations, the first and second bodies 402, 404 may be coupled together by a plurality of fasteners. In such a variation, the plurality of fasteners may be arranged in any manner suitable to securely couple the first and second bodies 402, 404 together. For example, the plurality of fasteners may be arranged collinearly, such as along a longitudinal and/or lateral dimension. The plurality of fasteners may be arranged such that each fastener 460 may avoid any fluid pathway, valve, bubble trap, or other component of the first end panel 400. One or more seals may be positioned between the two bodies 402, 404, such that a fluid-tight seal may be formed between the two bodies 402, 404. Accordingly, the first end panel 400 may comprise a cohesive, fluid-tight body. In some variations, the first end panel 400 may be integrally formed, such that the fastener 460 may not be required.

Figure 5B:
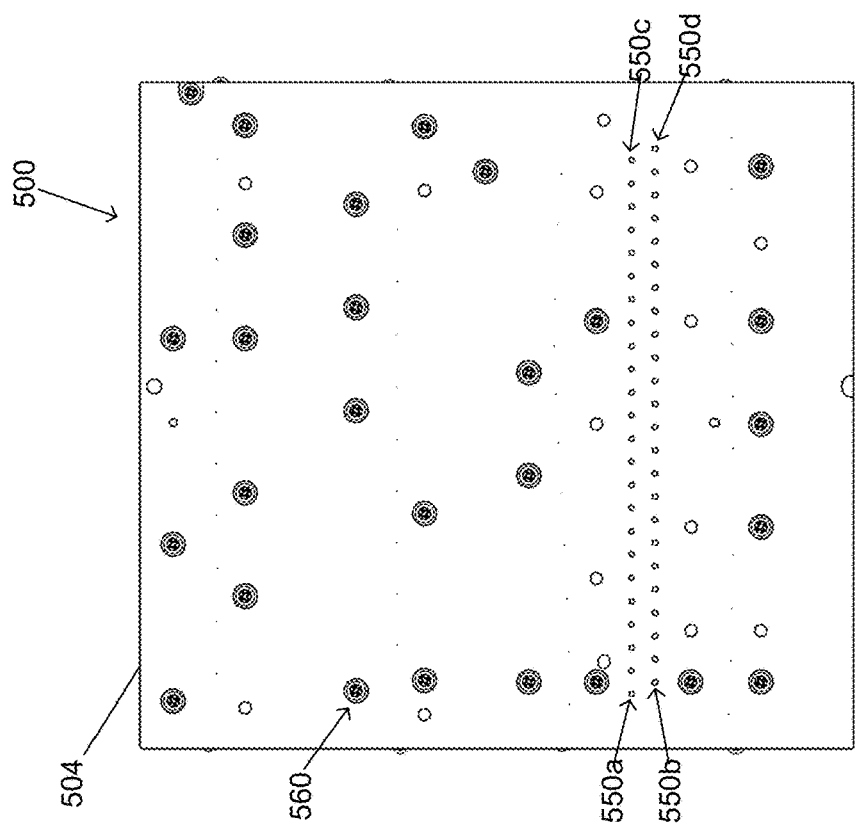
FIG. 5B shows a rear view of the first end panel shown in FIG. 5A.
Figure 5A:
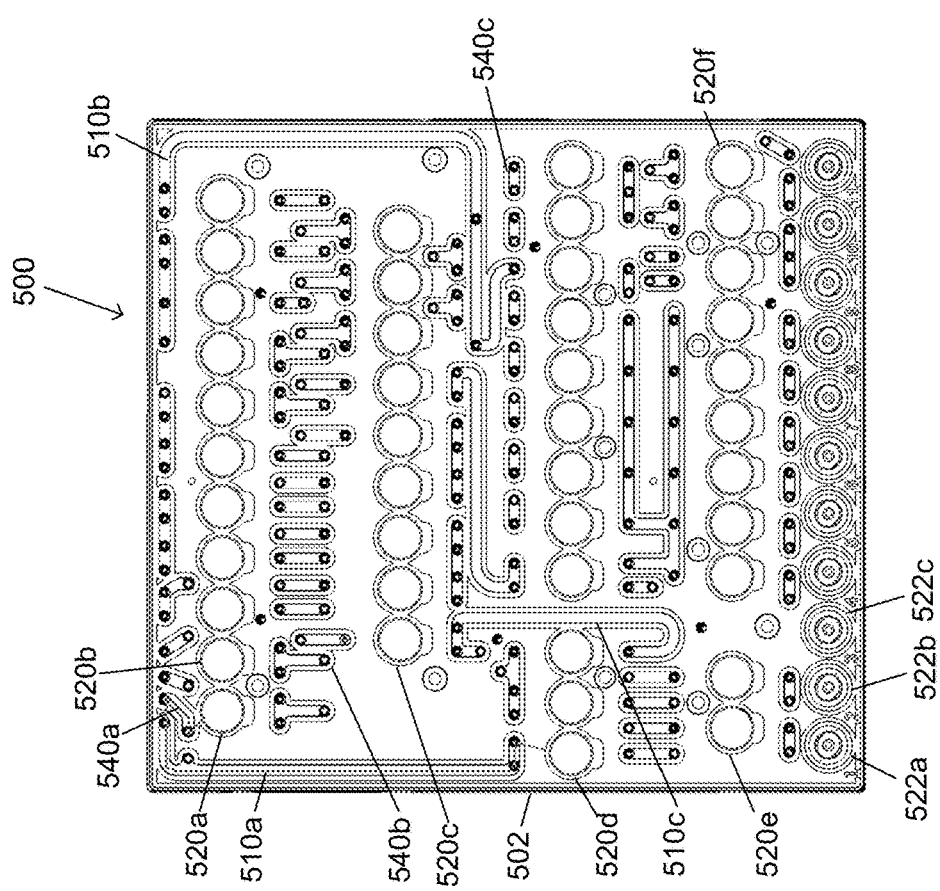
FIG. 5A shows a front view of an illustrative variation of a second end panel of a fluidic manifold.
Figure 5C:
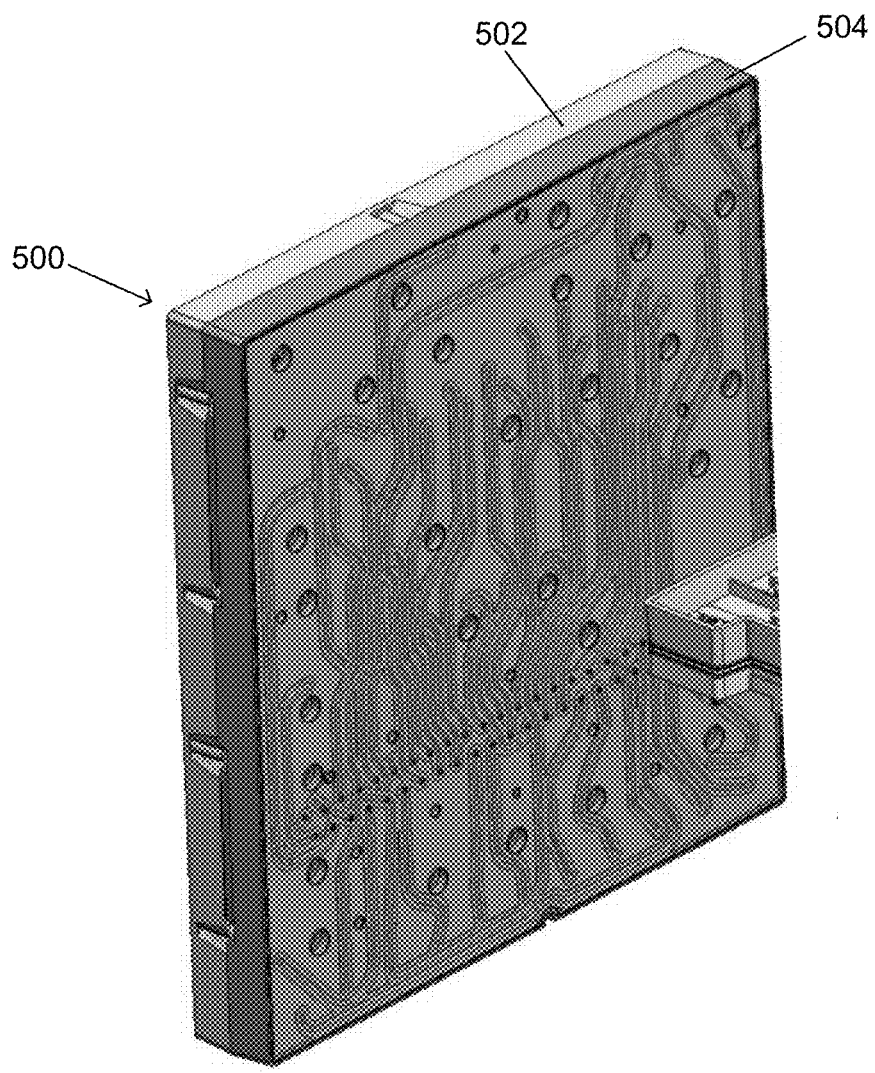
FIG. 5C shows a perspective view of the first end panel shown in FIG. 5A.

FIGS. 5A-5C show a second end panel 500. The second end panel 500 may comprise a plurality of fluidic pathways 510a-510c, a plurality of valves 520a-520f, a plurality of fluid extraction ports 522a-522c, a plurality of windows 540a-540c, a plurality of outlet ports 550a-550d, and a fastener 560. FIG. 5A shows a first body 502 of the second end panel 500. The first body 502 of the first end panel 500 may define one or more fluid pathways, such as a first fluid pathway 510a, a second fluid pathway 510b, a third fluid pathway 510c, and so on. The fluid pathways of the first body 502 of the first end panel 500 may be covered by a film (not shown). The film may be similar to the description provided in reference to FIGS. 4A-4C. Similarly, the descriptions for the fluidic pathways 510a-510c, the plurality of valves 520a-520f, and the plurality of windows 540a-540c may correspond to the descriptions of the fluidic pathways 410a-410c, valves 420a-420f, and windows 440a-440c provided in reference to FIGS. 4A-4C.

The first body 502 may further comprise the plurality of fluid extraction ports 522a-522c. The fluid extraction ports 522a-522c may be configured for removing fluid from the fluidic pathways 510a-510c. For example, the fluid extraction ports 522a-522c may each comprise a needless injection port. The fluid extraction ports 522a-522c may form a fluid seal that may be impermeable to liquid and/or gas. The fluid seal may be temporarily broken (e.g., pierced) by a conduit and/or needle, such as a syringe. The fluid extraction ports 522a-522c may be configured to reform the fluidic seal after a fluid extraction process may be performed. The fluid extraction ports 522a-522c may be arranged collinearly, such that the fluid extraction ports 522a-522c may be arranged along a line extending from a first side of the first body 502 to a second side of the first body 502. In some variations, there may be 11 fluid extraction ports that may be arranged collinearly.

Fluid may flow through the fluidic pathways, valves, and windows of the second end panel 500 in a variety of routes. That is, the plurality of valves 520a-520f may be used to direct (e.g., control) the fluid according to a desired route. For example, as shown in FIG. 5A, the valve 520a may be fluidically connected to the window 540a. The window 540a may be fluidically connected to the fluidic pathway 510a. Accordingly, fluid may flow through the valve 520a to the fluidic pathway 510a, past the window 540a, when the valve 520a is in an open position. In some variations, the valve 520a may be actuated (e.g., via a controller) to a closed position, such that fluid may not flow to the fluidic pathway 510a. Fluid may flow along the fluidic pathway 510a to the valve 520d. Similarly, the position (e.g., open or closed) of the valve 520d may determine whether fluid may flow therethrough. The valve 520d may be fluidically connected to an outlet port, such as the outlet port 550c. Accordingly, fluid may flow from the valve 520a to the outlet port 550c. Alternative routes may be achieved by the positions of any of the valves of the second end panel 500 according to one or more valve actuation inputs provided by the controller.

FIG. 5B shows a second body 504 of a second end panel 500. The second body 504 may comprise the plurality of outlet ports 550a-550d. The description of the plurality of outlet ports 550a-550d may correspond to the description of the outlet ports 450a-450d provided in reference to FIGS. 4A-4C. In some variations, the second body 504 may comprise one or more fluidic pathways, which may correspond to the description provided for the fluidic pathways of the first body 502. The two bodies 502, 504 of the second end panel 500 may be coupled together. For example, the first and second bodies 502, 504 may be coupled together by the fastener 560. The description of the coupling of the two bodies 502, 504 and the fastener 560 may correspond to the description of the coupling of the two bodies 402, 404 and the fastener 460 provided in reference to FIGS. 4A-4C.

b. Central Panel

The fluidic manifold described herein may comprise one or more central panels. The central panel may comprise one or more fluidic pathways. For example, the central panel may be configured to transfer fluid via the fluidic pathways to and/or from end panels and/or one or more modules of the cartridge. The central panel may be coupled to one or more end panels. The fluidic pathways of the central panel may be fluidically connected to one or more fluidic pathways of the end panel(s). In some variations, the central panel may comprise a cross-sectional shape such as rectangular, a triangle, a square, a trapezoid, a circle, or a combination thereof. In some variations, there may be between 1 and 10 central panels, 1 and 6 central panels, or 1 and 4 central panels, including 1, 2, 3, or 4 central panels.

Figure 6A:
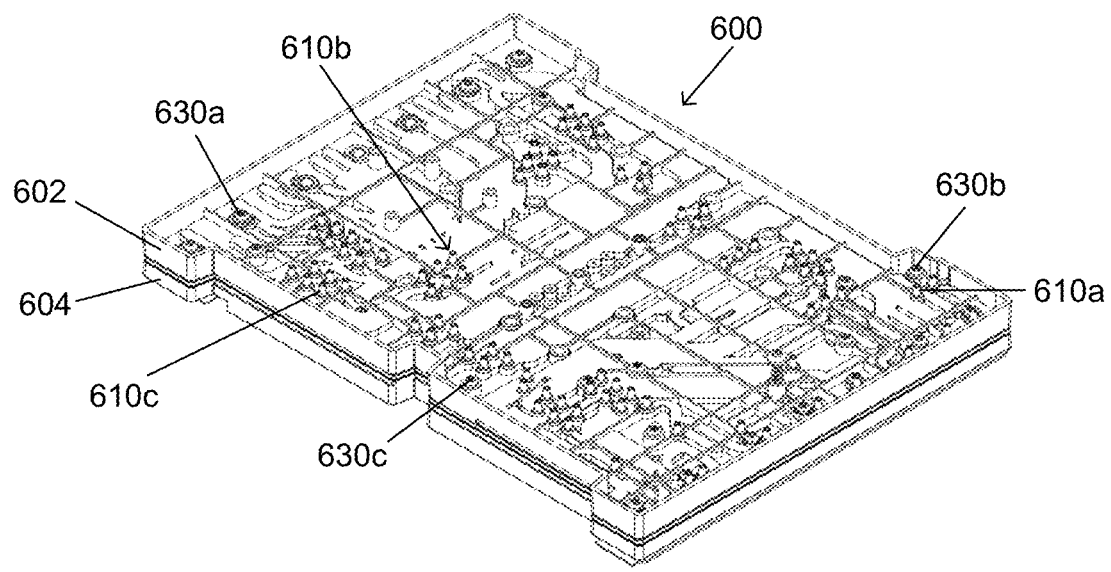
FIG. 6A shows a front perspective view of an illustrative variation of a central panel of a fluidic manifold.
Figure 6B:
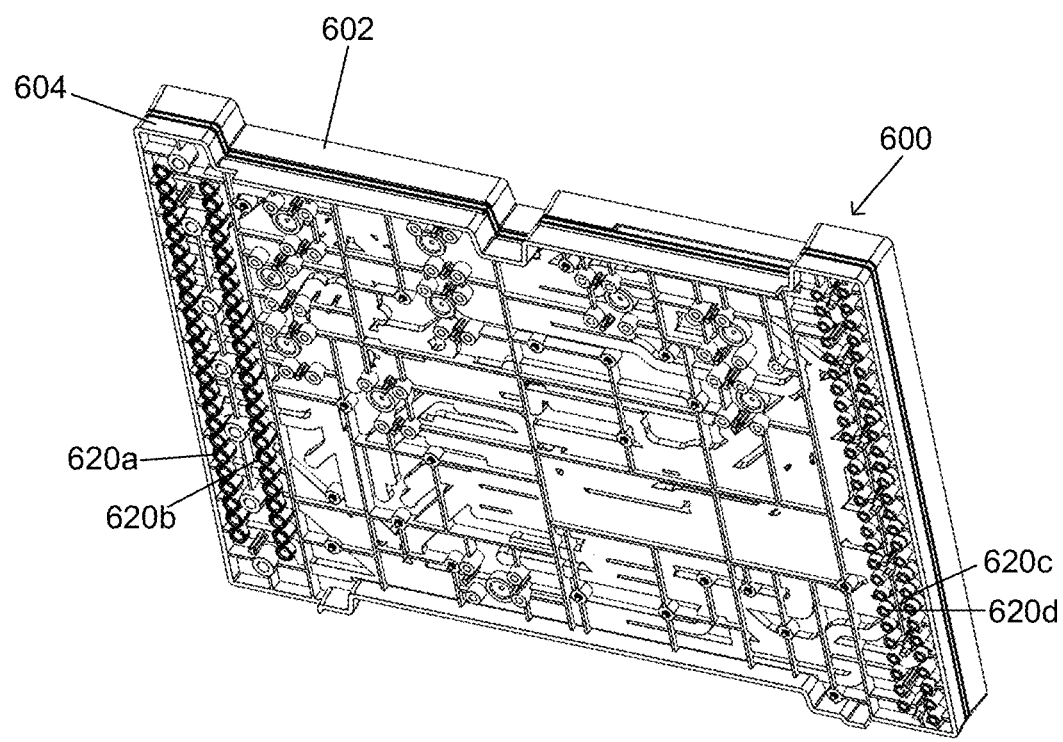
FIG. 6B shows a rear perspective view of the central panel shown in FIG. 6A.

FIGS. 6A and 6B show an illustrative variation of a central panel 600. The central panel 600 may comprise a first body 602, a second body 604, and a middle body 606. The middle body 606 may form a layer between the first and second bodies 602, 604. The first and second bodies 602, 604 may define one or more fluid ports configured for fluid transfer. For example, the first body 602 may comprise a plurality of fluid transfer ports, such as the fluid transfer ports 610a-610c, which may be configured to receive fluid from another module and/or transfer fluid to another module. Accordingly, the fluid transfer ports 610a-610c may be configured for bidirectional fluid flow. As shown in FIG. 6A, the fluid transfer ports 610a-610c may be arranged on the first body 602 of the central panel 600. Additionally, or alternatively, the second body 604 may define one or more fluid ports configured for fluid transfer. For example, the second body 604 may comprise a plurality of bridge transfer ports, such as bridge transfer ports 620a-620d as shown in FIG. 6B. The bridge transfer ports 620a-620d may be configured to receive fluid from a bridge and/or transfer fluid to a bridge.

Figure 6C:
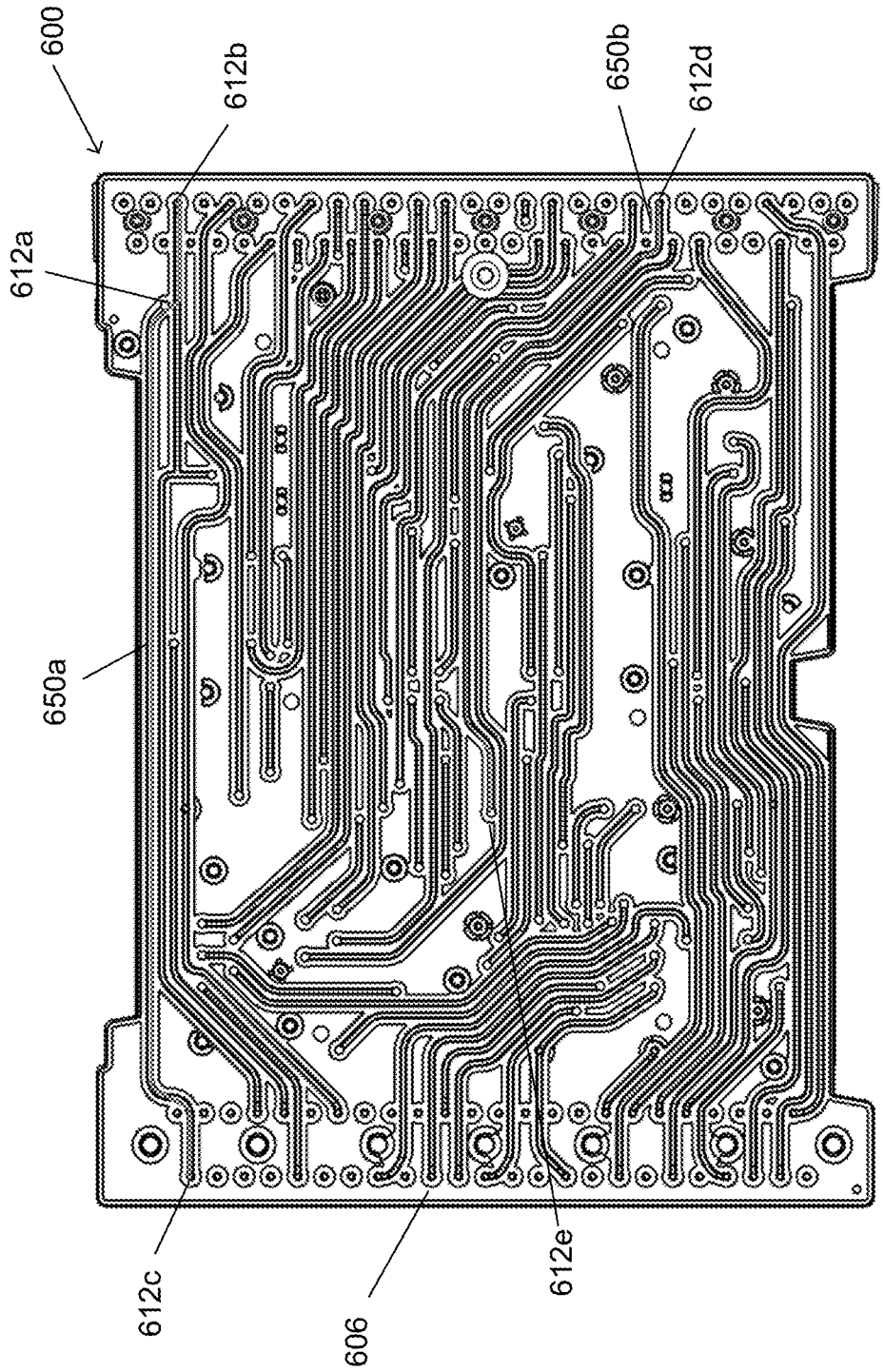
FIG. 6C shows a front view of an illustrative variation of a middle body of the central panel shown in FIG. 6A.

FIG. 6C shows an illustrative variation of the middle body 606. The middle body 606 may define a plurality of fluidic pathways and a plurality of fluid openings. For example, the middle body 606 may comprise a first fluidic pathway 650a, a second fluidic pathway 650b, and so on. The plurality of openings may correspond to one or more transfer ports. For example, a first fluid opening 612a may correspond to a fluid transfer port and a second fluid opening 612b may correspond to a bridge transfer port. Accordingly, the fluidic pathways of the middle body 606 may be fluidically connected to one or more modules and/or one or more bridges. In some variations, a fluidic pathway of the middle body 606 may be fluidically connected to both of a fluid transfer port and a bridge transfer port. For example, the fluidic pathway 650a may be fluidically connected to the fluid openings 612a, 612b, 612c. The fluid openings 612b, 612c may correspond to bridge transfer ports, while the fluid opening 612a may correspond to a fluid transfer port. Accordingly, as shown in FIG. 6C, fluid may flow from the fluid opening 612b (which may fluidically connected to a bridge transfer port of a first bridge), along the fluidic pathway 650a, and to the fluid opening 612c (which may be connected to a bridge transfer port of a second bridge). The fluidic pathway 650a may also be fluidically connected to the fluid opening 612a, which may be fluidically connected to a fluid transfer port. Accordingly, fluid may be transferred to and/or from the fluidic pathway 650a through any of the fluid openings 612a-c. In another example, the fluidic pathway 650b may be fluidically connected to the fluidic openings 612d (which may fluidically connected to another bridge transfer port of a first bridge) and 612e (which may be fluidically connected to a fluid transfer port). Accordingly, fluid may be transferred to and/or from the fluidic pathway 650b through either of the fluid openings 612a, 612b. In this way, fluid may travel between bridges and/or one or more modules via the fluidic pathways of the middle body 606.

In some variations, the first body 602, second bod 604, and middle body 606 may be coupled together by a mechanical fastener (e.g., screws, nails, bolts), an adhesive (e.g., glue), a friction fit (e.g., a protrusion of one component received within a corresponding opening of another component), or a combination thereof. For example, the bodies 602, 604, 606 may be coupled together by the fasteners 630a-630c. That is, the fasteners 630a-630c may extend through each of the bodies 602, 604, 606 such that the first and second bodies 602, 604 may be securely coupled on either side of the middle body 606. The fasteners 630a-630c may be arranged in any manner suitable to securely couple the bodies 602, 604, 606 together. For example, the fasteners 630a-630c may be arranged proximal to an outer edge of each of the first and second bodies 602, 604. In another example, the plurality of fasteners may be arranged such that each fastener avoids any fluidic pathway of the central panel 600.

In some variations, a degassing module and/or vent manifold may be coupled to the central panel. For example, the degassing module and/or vent manifold may be mechanically fastened to the central panel and/or may be fluidically connected to the central panel. Accordingly, fluid may flow through the central panel, through one or more the degassing module and/or vent manifold, and subsequently flow back to the central panel.

Figure 7B:
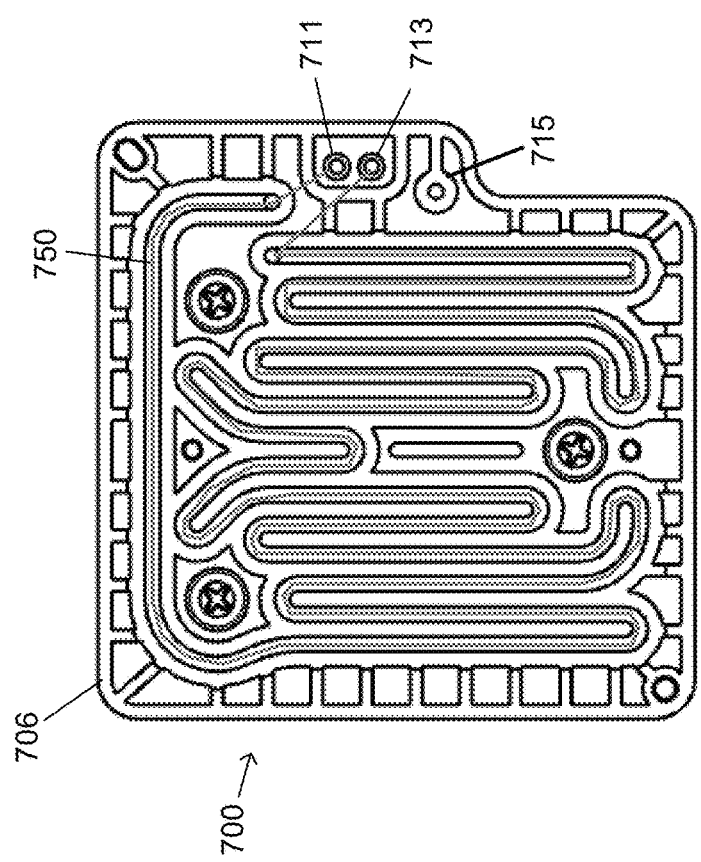
FIG. 7B shows a front view of a middle body of the degassing module shown in FIG. 7A.
Figure 7A:
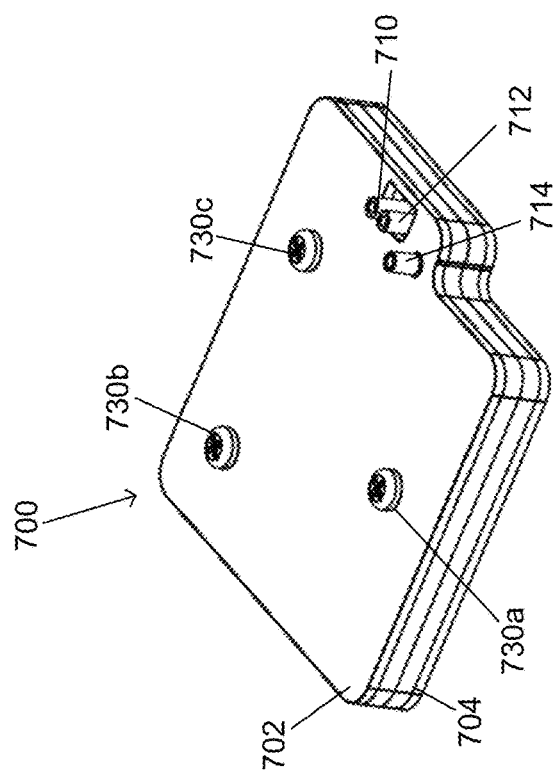
FIG. 7A shows a front perspective view of an illustrative variation of a degassing module of a fluidic manifold.

FIGS. 7A-7B show a degassing module 700. The degassing module 700 may comprise a first body 702, a second body 704, and a middle body 706. The first body 702 may comprise a plurality of fluid transfer ports. For example, the first body 702 may comprise an inlet port 710, an outlet port 712, and a gas port 714. The inlet port 710 may be configured to receive fluid, such as from fluid conduit coupled to a fluid transfer port of the central panel. The outlet port 712 may be configured to transfer fluid (e.g., a liquid) out of the degassing module 700, such as to a fluid conduit coupled to a fluid transfer port of the central panel. The gas port 714 may be configured to provide another fluid (e.g., a gas), such as to a fluid transfer port of the central panel.

The ports may be fluidically connected to one or more openings. For example, the middle body 706 may comprise an inlet opening 711, an outlet opening 713, and a gas opening 715. The inlet opening 711 may be fluidically connected to the inlet port 710. Accordingly, fluid may flow through the inlet port 710, into the fluid opening 711, and to the fluidic pathway 750. The outlet opening 713 may be fluidically connected to the outlet port 712. Accordingly, fluid may flow from the fluidic pathway 750, into the outlet opening 713, and through the outlet port 712. The fluidic pathway 750 may define a tortuous path. For example, as shown in FIG. 7B, the fluidic pathway 750 may comprise a plurality of bends.

While fluid may flow along the fluidic pathway 750, a gas may be extracted from the fluid. For example, a gas opening 715 may be fluidically connected to the fluidic pathway 750. The gas opening 715 may be separated from the fluidic pathway 750 by a membrane, such as a gas permeable membrane (not shown). Accordingly, a gas may be transferred through the gas opening 715 to the gas port 714. The gas port 714 may be coupled to a fluid conduit (e.g., tube) configured to apply a suction. That is, the gas port 714 may facilitate a degassing processing by providing a flow path for gases removed from the fluid flowing along the fluidic pathway 750.

The bodies 702, 704, 706 may be coupled together to form a fluid-tight seal. For example, the bodies 702, 704, 706 may be coupled together by the fasteners 730a-730c. That is, the fasteners 730a-730c may extend through each of the bodies 702, 704, 706 such that the first and second bodies 702, 704 may be securely coupled on either side of the middle body 706. The fasteners 730a-730c may be arranged in any manner suitable to securely couple the bodies 702, 704, 706 together. For example, the fasteners 730a-730c may be arranged such that each fastener avoids any fluidic pathway of the middle body 706.

Figure 8A:
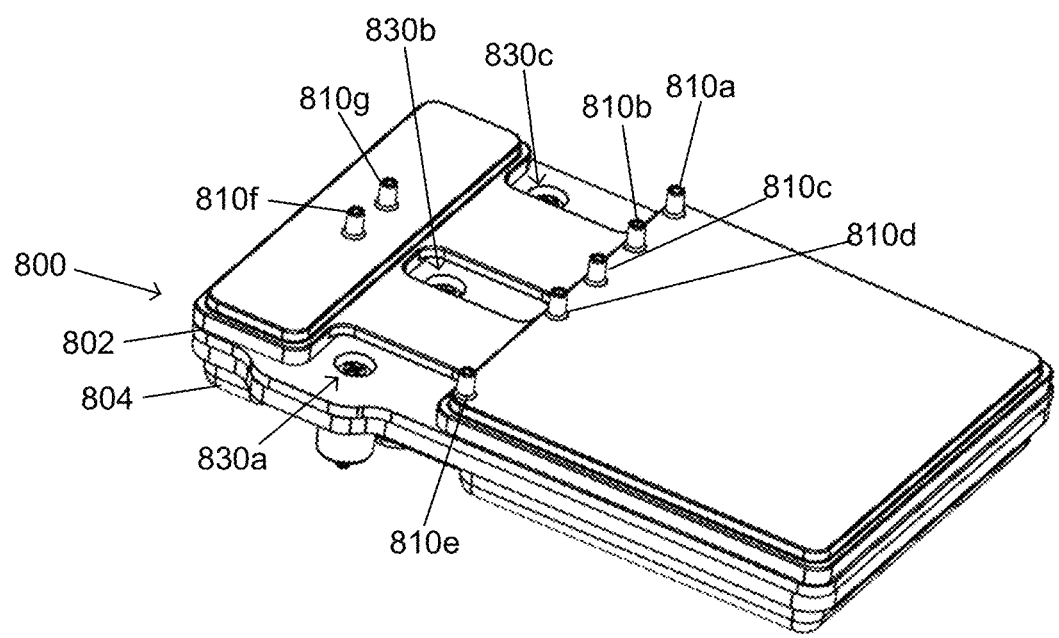
FIG. 8A shows a front perspective view of an illustrative variation of a vent manifold of a fluidic manifold.
Figure 8B:
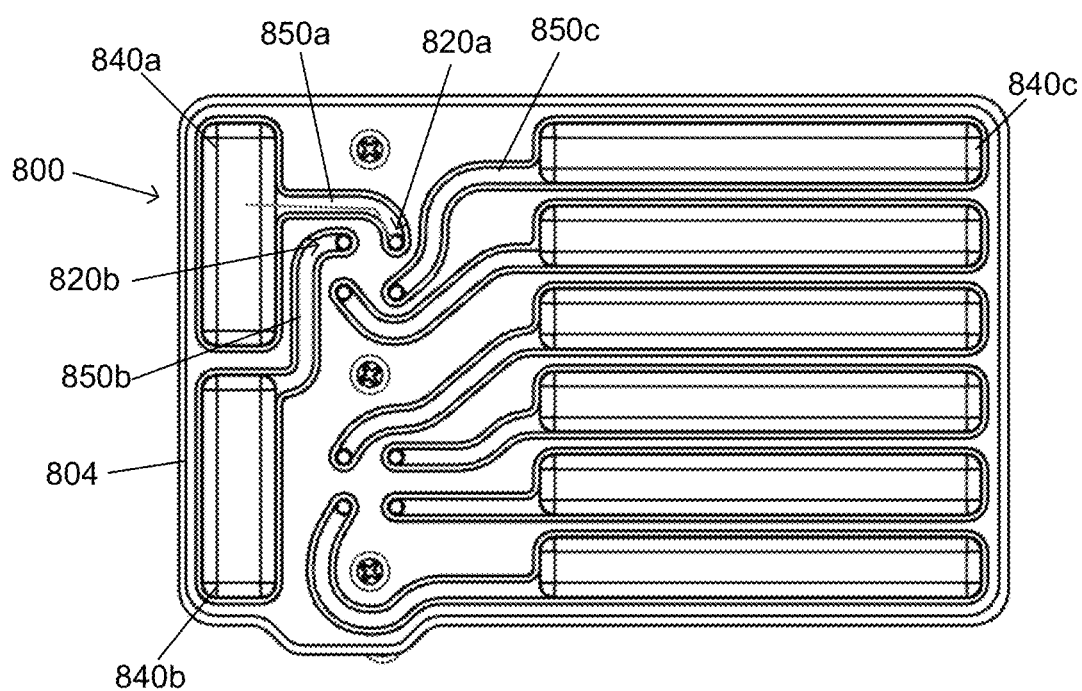
FIG. 8B shows a front view of a middle body of the vent manifold shown in FIG. 8A.

FIGS. 8A-8B show a vent manifold 800. The vent manifold 800 may comprise a first body 802 and a second body 804. The first body 802 may comprise a plurality of fluid transfer ports, such as a first fluid transfer port 810a, a second fluid transfer port 810b, and so on. The second body 804 may comprise a plurality of fluid channels (e.g., fluid cavities), such as a first fluid channel 840a, a second fluid channel 840b, a third fluid channel 840c, and so on. The second body 804 may further comprise a plurality of fluidic pathways and a plurality of fluid openings. For example, the second body 804 may comprise a first fluidic pathway 850a, a second fluidic pathway 850b, a third fluidic pathway 850b, and so on. Similarly, the second body 804 may comprise a first fluid opening 820a, a second fluid opening 820b, a third fluid opening 820c, and so on. In some variations, positioned between the first and second bodies 802, 804 may be a filter. That is, the filter may be positioned within the flow path between the fluid channels and the fluid transfer ports. The filter may be configured to remove particles within a fluid flowing through the vent manifold. The first and second bodies 802, 804 may be coupled by a plurality of fasteners, such as the fasteners 830a-830c. The fasteners 830a-830c may be positioned such that the fluidic pathways, ports, and channel described herein are avoided. In some variations, there may be a seal between the first and second bodies 802, 804 such that the coupling is fluid tight.

The fluid transfer ports, fluid openings, fluidic pathways, and fluid channels may be fluidically connected. For example, the first fluid channel 840a may be fluidically connected to the first fluid transfer port 810a. The first fluid transfer port 810 may be coupled to a fluid conduit that may be coupled to a module of the cartridge or another fluid transfer port of the central panel. The first fluid transfer port 810a may also be fluidically connected to the fluid transfer opening 820a, which in turn may be fluidically connected to the fluidic pathway 850a. Therefore, fluid may flow to and/or from another fluidic pathway of the central panel via a fluid conduit coupled to the first fluid transfer port 810a. In this way, the vent manifold may perform a venting process by transferring a gas (e.g., sterile air) to one or more fluidic pathways of the central panel. The gas may release any particles that may have clogged the filter of the vent manifold and/or remove any condensed fluid within the fluidic pathway(s) of the central panel.

c. Bridge

One or more components of the fluidic manifold may be coupled via abridge. The bridge may comprise one or more fluidic pathways, such that the coupled components may be fluidically connected. For example, an end panel may be fluidically connected to a central panel via a first bridge. The central panel may be coupled to more one than bridge, such that more than one end panel may be fluidically connected to the central panel. The size and/or quantity of the bridge may correspond to the central panel. For example, the bridge may comprise a lateral dimension (e.g., width) equivalent to a lateral dimension of the central panel. In some variations, the lateral dimension of the bridge may correspond to only a portion of the lateral dimension of the central panel. The quantity of bridges may correspond to the shape of the central panel, in that each end of the central panel may be configured to receive a bridge. For example, a central panel comprising 4 ends may be configured to receive up to 4 bridges. In some more variations, more than one bridge may be coupled to a single end of the central panel. For example, in some variations, there may be between 1 and 10 bridges, 1 and 6 bridges, or 1 and 4 bridges, including 1, 2, 3, 4, 5, 6, 7, 8, 9, or 10 bridges.

FIGS. 9A-9E show an illustrative variation of a first bridge 900. The first bridge 900 may comprise a plurality of fluid transfer ports, such that the first bridge 900 may be fluidically connected to one or more of a central panel and an end panel. For example, as shown, the first bridge 900 may comprise a plurality of central panel transfer ports, such as a first central panel transfer port 910a, a second central panel transfer port 910b, and so on. The first bridge may also comprise a plurality of end panel transfer ports, such as a first end panel transfer port 920a, a second end panel transfer port 920a, and so on. The central panel transfer ports 910a, 910b may be configured to fluidically connect to the bridge transfer ports of a central panel, such as the bridge transfer ports 620a-6260d described in reference to FIG. 6B. For example, the transfer ports 910a may fluidically connect to a bridge transfer port. There may be a seal between the central panel transfer ports 910a, 910b and the respective bridge transfer ports, such that a sterile fluid transfer may occur therebetween. The central panel transfer ports 910a, 910b may be configured for bidirectional fluid flow, such that fluid may flow from a central panel to the bridge 900, or vice versa. The end panel transfer ports 920a, 920b may be configured to fluidically connect to the outlet ports of an end panel, such as the outlet ports 450a-450d described in reference to FIG. 4B or the outlet ports 550a-550d described in reference to FIG. 5B. For example, the end panel transfer ports 920a, 920b may fluidically connect to an outlet port. There may be a seal between the end panel transfer ports 920a, 920b and the respective outlet ports, such that a sterile fluid transfer may occur therebetween. The end panel transfer ports 920a, 920b may be configured for bidirectional fluid flow, such that fluid may flow from an end panel to the bridge 900, or vice versa.

The first bridge 900 may be securely coupled to a central panel and/or an end panel. For example, the first bridge 900 may comprise a plurality of openings configured to receive a mechanical fastener configured to couple the first bridge 900 to the central panel, and may, additionally or alternatively, comprise a plurality of openings configured to receive a mechanical fastener configured to couple the first bridge 900 to the end panel. In some variations, the first bridge may comprise a plurality of central panel fastener openings, such as a first central panel fastener opening 940a, a second central panel fastener opening 940b, a third central panel fastener opening 940c, and so on. Accordingly, a mechanical fastener (e.g., screw, nail, bolt) may extend from or through a central panel to the central panel fastener opening to securely couple the first bridge to the central panel. In some variations, additional or alternative means for coupling the first bridge to the central panel may be used, such as an adhesive (e.g., glue). Similarly, the first bridge may comprise a plurality of end panel fastener openings, such as a first end panel fastener opening 930a, a second end panel fastener opening 930b, a third end panel fastener opening 930c, and so on. A mechanical fastener (e.g., screw, nail, bolt) may extend from or through an end panel to the end panel fastener opening to securely couple the first bridge to the end panel. In some variations, additional or alternative means for coupling the first bridge to the end panel may be used, such as an adhesive (e.g., glue).

Figure 9A:
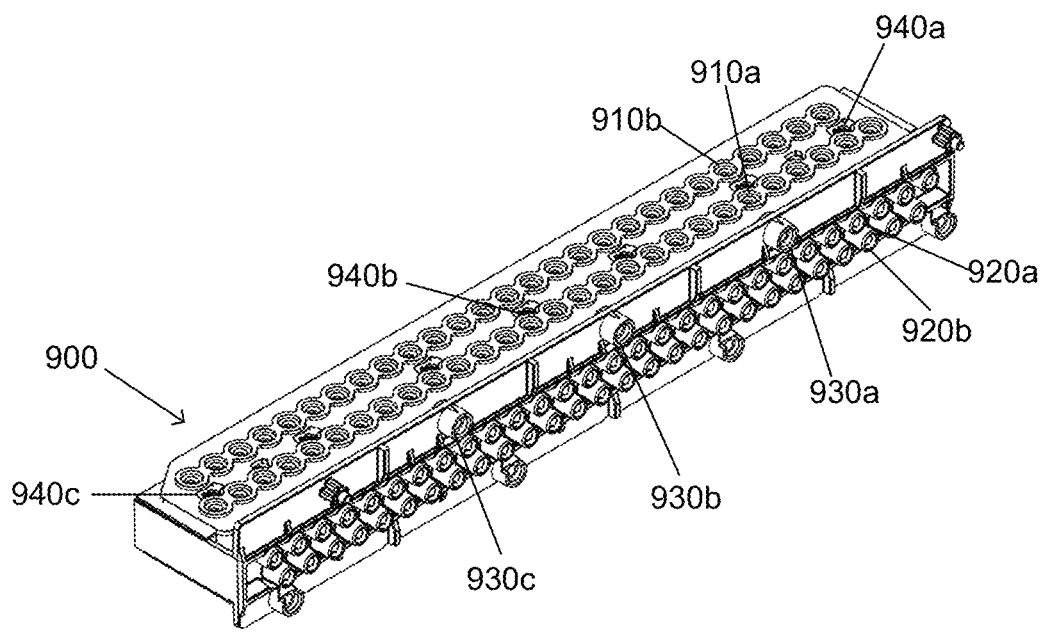
FIG. 9A shows a front perspective view of an illustrative variation of a first bridge of a fluidic manifold.
Figure 9B:
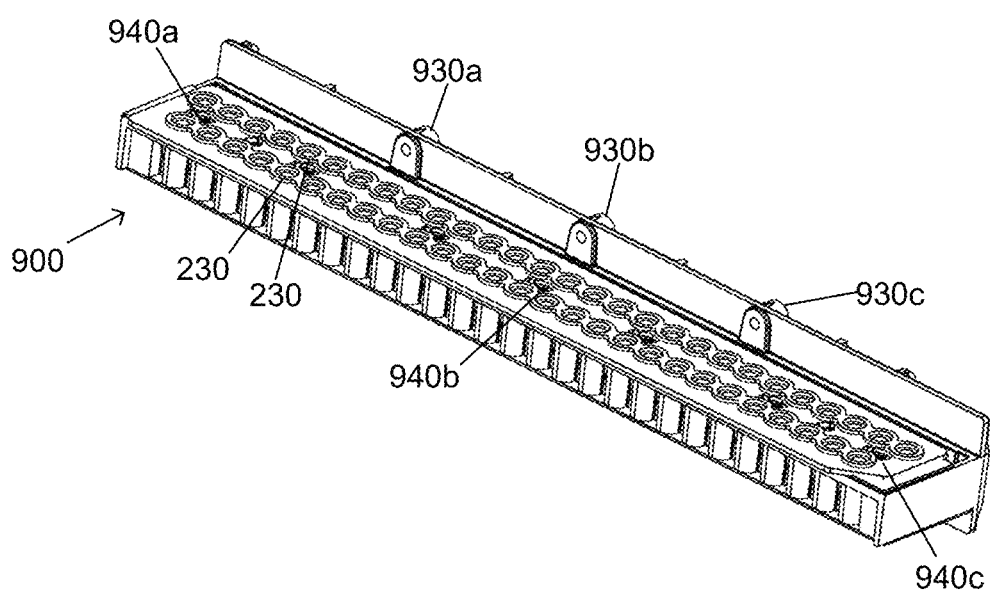
FIG. 9B shows a rear perspective view of the first bridge shown in FIG. 9A.
Figure 9C:
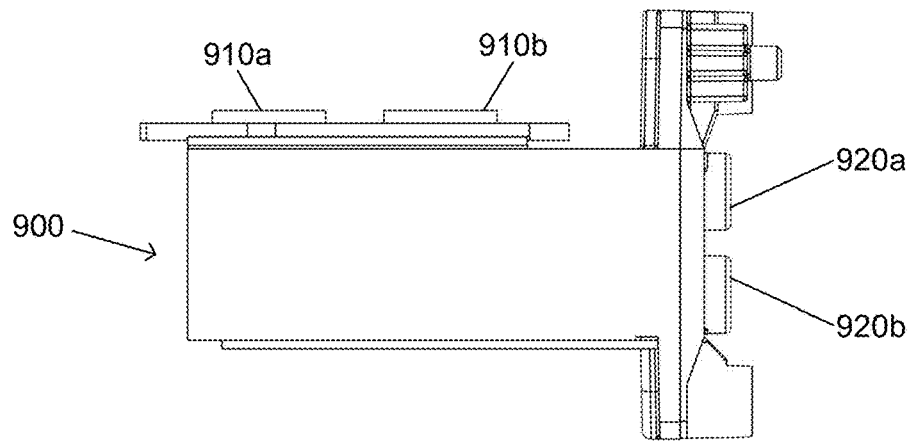
FIG. 9C shows a side view of the first bridge shown in FIG. 9A.
Figure 9D:
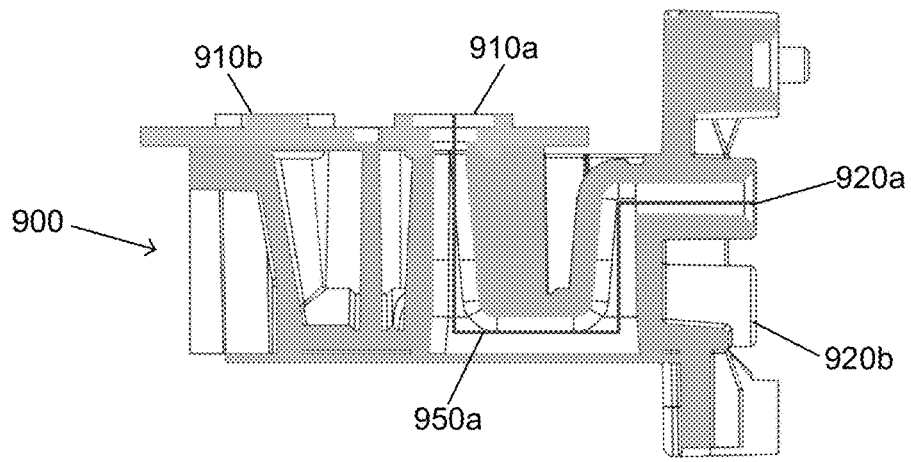
FIGS. 9D and 9E show illustrative variations of a fluidic pathway of the first bridge shown in FIG. 9A.
Figure 9E:
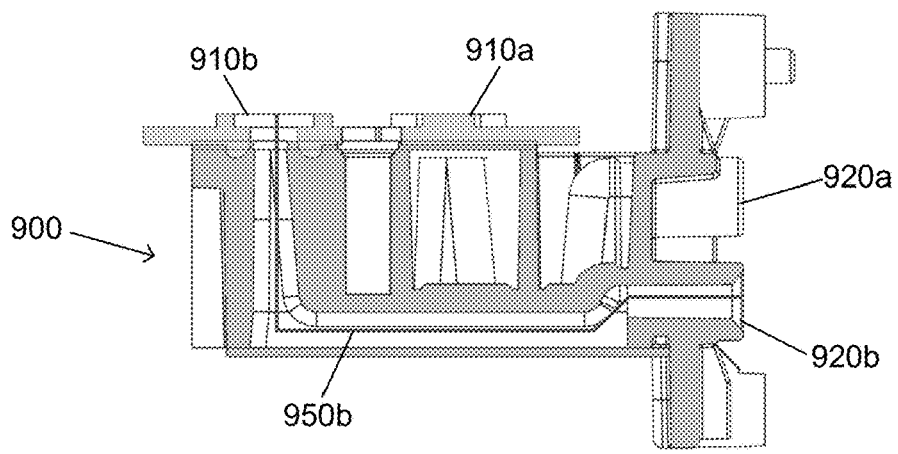

The first bridge 900 may comprise one or more fluidic pathways. For example, FIGS. 9D and 9E show variations of fluidic pathways of the first bridge 900. The fluidic pathways of the first bridge 900 may be defined by a groove, a depression, or a channel. The fluidic pathways may comprise a cross-sectional shape suitable for transporting a fluid, such as a circle, a square, a triangle, a trapezoid, or a combination thereof. For example, FIG. 9D shows an illustrative variation of a first fluidic pathway 950a of the first bridge 900. The first fluidic pathway 950a may extend from the first central transfer port 910a to the first end panel transfer port 920a. The first fluidic pathway 950a may comprise a circular cross-section with one or more bends. Accordingly, the central panel may be fluidically connected to the end panel via the fluidic pathway 910a. In another example, FIG. 9E shows an illustrative variation of a second fluidic pathway 950b of the first bridge 900. The second fluidic pathway 950b may extend from the second central transfer port 910b to the second end panel transfer port 920b. The second fluidic pathway 950b may comprise a circular cross-section with one or more bends. Accordingly, the central panel may be fluidically connected to the end panel via the fluidic pathway 910b. The fluidic pathways 950a, 950b may be used simultaneously or, in some variations, may not be. The fluidic pathways 950a, 950b may be fluidically isolated from one another, such that fluid may not mix between the fluidic pathways 950a, 950b.

FIGS. 10A-10E show an illustrative variation of a second bridge 1000. The second bridge 1000 may comprise a plurality of fluid transfer ports similar to those described in reference to FIGS. 9A-9E. For example, the second bridge 1000 may comprise a plurality of central panel transfer ports, such as a first central panel transfer port 1010a, a second central panel transfer port 1010b, and so on. The description of the central panel transfer ports 1010a, 1010b may correspond to the description provided for the central panel transfer ports 910a, 910b in reference to FIGS. 9A-9E. In another example, the second bridge 1000 may comprise a plurality of end panel transfer ports, such as a first end transfer port 1020a, a second end transfer port 1020b, and so on. The description of the end panel transfer ports 1020a, 1020b may correspond to the description provided for the end panel transfer ports 920a, 920b in reference to FIGS. 9A-9E.

The second bridge 1000 may be securely coupled to a central panel and/or an end panel in a similar fashion as described for the first bridge 900. For example, the second bridge 1000 may comprise a plurality of openings configured to receive a mechanical fastener configured to couple the second bridge 1000 to the central panel, and may, additionally or alternatively, comprise a plurality of openings configured to receive a mechanical fastener configured to couple the second bridge 1000 to the end panel. That is, in some variations, the second bridge 1000 may comprise a plurality of central panel fastener openings, such as a first central panel fastener opening 1040a, a second central panel fastener opening 1040b, a third central panel fastener opening 1040c, and so on. The description of the central panel fastener openings 1040a-1040c may correspond to the description provided for the central panel fastener openings 940a-940c in reference to FIGS. 9A-9E. Similarly, the second bridge 1000 may comprise a plurality of end panel fastener openings, such as a first end panel fastener opening 1030a, a second end panel fastener opening 1030b, a third end panel fastener opening 1030c, and so on. The description of the end panel fastener openings 1030a-1030c may correspond to the description provided for the end panel fastener openings 930a-930c in reference to FIGS. 9A-9E.

Figure 10A:
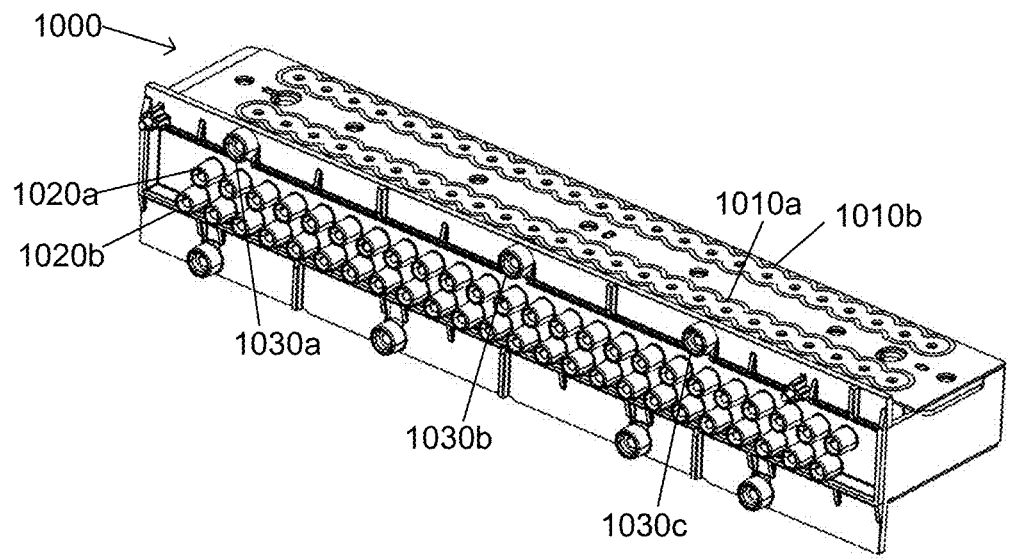
FIG. 10A shows a front perspective view of an illustrative variation of a second bridge of a fluidic manifold.
Figure 10B:
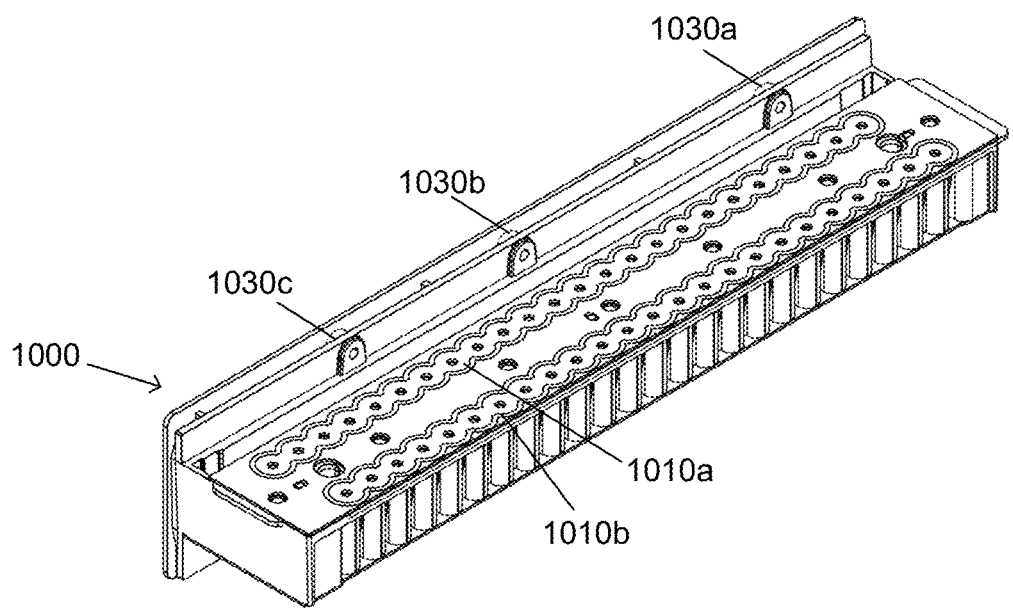
FIG. 10B shows a rear perspective view of the second bridge shown in FIG. 10A.
Figure 10C:
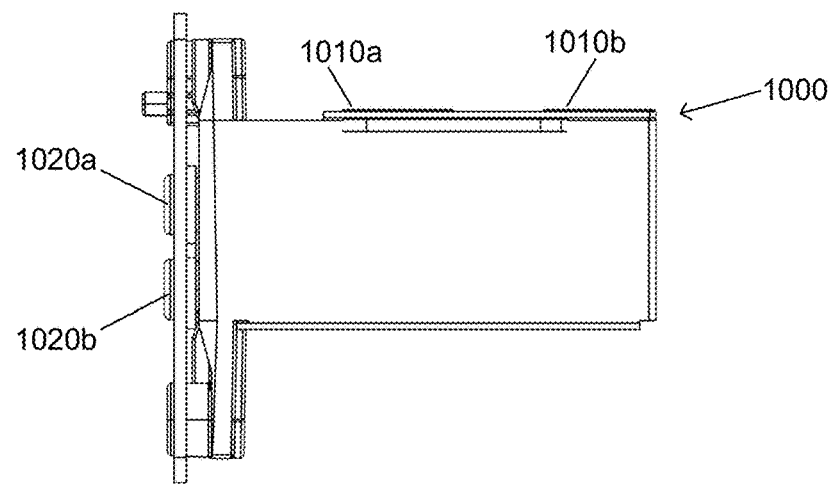
FIG. 10C shows a side view of the second bridge shown in FIG. 10A.
Figure 10D:
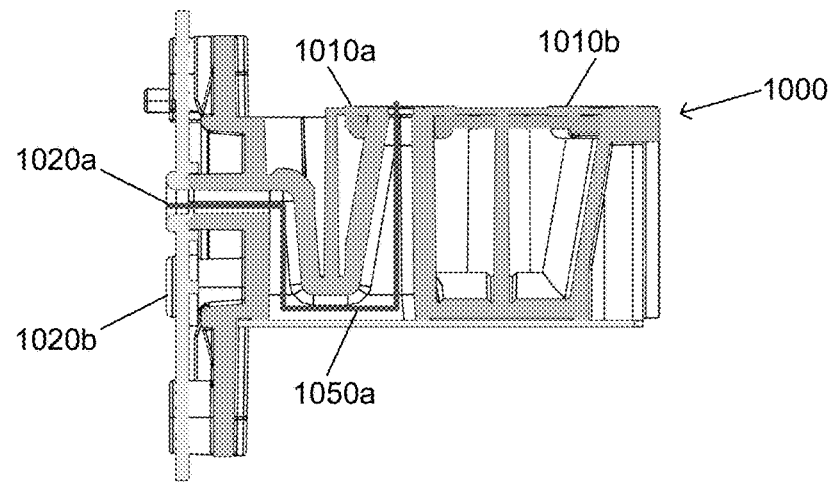
FIGS. 10D and 10E show illustrative variations of a fluidic pathway of the second bridge shown in FIG. 10A.
Figure 10E:
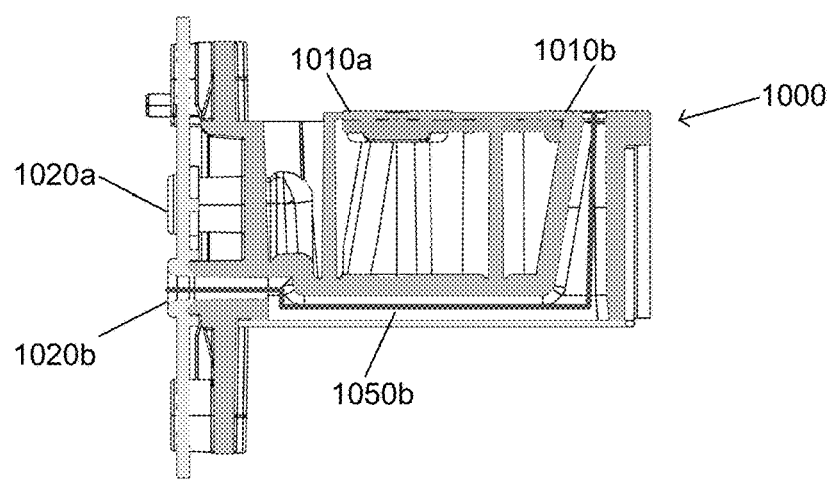

The second bridge 1000 may comprise one or more fluidic pathways. FIGS. 10D and 10E show variations of fluidic pathways of the second bridge 1000. For example, the second bridge may comprise a first fluidic pathway 1050a and a second fluidic pathway 1050b. The description of the first and second fluidic pathways 1050a, 1050b may correspond to the descriptions provided for the first and second fluidic pathways 950a, 950b in reference to FIGS. 9D and 9E.

II. Methods of Fluid Control

Generally, the fluid control system described herein may facilitate one or more cell processing methods in an automated cell processing workcell by controlling the flow of fluid to one or more modules of the cell processing workcell. The control of fluid may be performed according to a pre-determined workflow. The workflow may be pre-programmed by a user via a controller of the workcell. The fluidic manifold may be controlled to deliver fluid to the one or more modules according to any workflow. The fluidic manifold may be fluidically linked to multiple fluid containers used to provide solutions or reagents, store cell products, or to collect waste solutions or reagents.

FIG. 11 provides a flowchart of an illustrative method of controlling fluid flow in an automated workcell. As shown, a method 1101 may include providing a fluid to a fluidic manifold of a cartridge 1110. For example, a fluid may comprise a solution (e.g., a cell solution, a cell suspension) having one or more of a cell, a media, a buffer, and a reagent. In some variations, the fluid may be provided to a fluid conduit (e.g., tube) fluidically connected to a valve of a first end panel or a second end panel. In further variations, the fluid may be provided to a fluid conduit fluidically connected to a fluid transfer port of a central panel. The fluid conduit may fluidically the fluidic manifold (e.g., first end panel, second end panel, central panel, degassing module, vent manifold) to another module of the cartridge or workcell. For example, the first end panel may be fluidically connected to a first bioreactor module of a bioreactor module and/or the second end panel may be fluidically connected to a second bioreactor module of the bioreactor module. The fluid conduits may be configured to optimally reduce the length, quantity, and/or diameter thereof, which may minimize entanglement of the fluid conduits.

The method 1101 may further include flowing the fluid through a fluidic pathway of one or more of a first end panel, a second end panel, and a central panel 1120. The fluidic pathway may be fluidically connected to a first bridge, which may be fluidically connected to the central panel. Accordingly, fluid may flow from the valve of the first end panel to the central panel. In some variations, fluid may flow in the opposite direction, such that fluid may flow from the central panel, through the fluidic pathways of the first bridge and first end panel, and may exit the fluidic manifold via the valve of the first end panel. The second end panel may be similarly fluidically connected to the central via the second bridge. In some variations, the central panel may be in direct fluidic communication with the first and/or second end panel, such that the fluidic pathways thereof may be fluidically connected without using a first and/or second bridge.

The method 1101 may further include performing a degassing process 1130. The degassing process may be performed by a degassing module. The degassing process may comprise removing a gas (e.g., air) from a liquid (e.g., a cell suspension). The gas may be dissolved in the liquid. In some variations, the gas may come out of solution due to a change in temperature. For example, a fluid may enter the fluidic manifold at a first temperature (e.g., about 4 degrees C.) and may subsequently rise to a second temperature (e.g., about 20 degrees C.) as the fluid flows through the fluidic manifold. As the gas comes out of solution, bubbles may form in the liquid, which may inhibit fluid flow through one or more fluidic pathways of the fluidic manifold and/or improperly trigger one or more sensors. Accordingly, the degassing process may remove the gas to facilitate fluid flow through the fluidic manifold.

The method 1101 may further include performing a venting process 1140. The venting process may be performed by a vent manifold. The vent manifold may be configured to transfer a gas (e.g., sterile air) from an external environment (e.g., outside of the cartridge and within the workcell) and transfer the gas to one or more fluidic pathways of the vent manifold and/or central panel. The gas may be contained in a fluid channel (e.g., fluid cavity) of the vent manifold, such that the gas may be selectively released into the fluidic pathway(s) to release any particles that may have clogged a filter of the vent manifold and/or remove any condensed fluid within the fluidic pathway(s). Advantageously, the transferred gas may increase a flow rate of the fluid flowing through the one or more fluidic pathways.

The method 1101 may further include measuring one or more parameters via a window of the first end panel 1150. For example, the window may be configured for optical detection, which may facilitate a measurement of the fluid. For example, the measurement may comprise a bubble count value. The bubble count value may be compared to a pre-defined condition, which may determine a response by the fluidic manifold. In some variations, the response may comprise routing the fluid through a bubble trap of the first end panel if the comparison indicates that the bubble count value meets or exceeds the pre-defined condition. In some variations, the second end panel may comprise a similar window that performs a similar function.

The method 1101 may further include measuring one or more parameters via a sensor of the central panel 1160. The sensor may comprise a pressure sensor. For example, the pressure sensor may measure a pressure value of a fluid flowing through one or more fluidic pathways of the central panel. The fluid may correspond to a fluid pump, such that the pressure sensor may indicate the performance of the pump in transferring fluid to or from the central panel. That is, the pressure sensor may indicate a flow rate of the fluid. For example, the pressure sensor may comprise a strain gauge that may deflect as fluid flows across the pressure sensor, such that the deflection may change a resistance value of the strain gauge. The resistance value may be correlated to a pressure value. The pressure value may be communicated to a flex circuit, which may compile the pressure values from multiple pressure sensors. The flex circuit may be in communication with a controller of the workcell.

The method 1101 may further include extracting fluid via a fluid extraction port 1170. The fluid extraction port, which may comprise a needless injection port, may provide an extraction path that may be used to quickly remove fluid from the fluidic manifold, such as in an emergency. An emergency may comprise a loss of electrical power, a leak elsewhere in the fluidic manifold, fluid stuck in or more locations of the fluidic manifold and/or cartridge, or another workflow interruption. The extraction process may be performed by opening (e.g., piercing) the fluid extraction port, extracting fluid, and closing the fluid extraction port. IN some variations, the fluid extraction port may close upon removal of an instrument, such as a syringe, that may have been used to initially open the fluid extraction port.

The method 1101 may further include transferring fluid to another module of the cartridge 1180. For example, the fluidic manifold may be fluidically connected to one or more modules of the cartridge. The fluidic connection(s) may facilitate one or more cell processing steps that may be performed in the one or more modules. Accordingly, the fluidic manifold may control the timing, sequencing, and/or duration of any cell processing step, by virtue of controlling fluid to or from the module performing the cell processing step. The fluidic manifold may automatically control the fluid according to a pre-determined workflow, which may be pre-determined by a controller of the workcell.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A cartridge for cell processing comprising:
a fluidic manifold comprising a first end panel, a second end panel, and a central panel connecting the first and second end panels, wherein each of the first and second end panels comprises a plurality of fluidic pathways molded therein and a plurality of valves for controlling fluid flow through the plurality of fluidic pathways.

2. The cartridge of claim 1, wherein the first end panel further comprises at least one window configured for optical detection.

3. The cartridge of claim 2, wherein the at least one window comprises a bubble sensing window.

4. The cartridge of claim 1, wherein the first end panel further comprises a bubble trap.

5. The cartridge of claim 1, wherein the second end panel further comprises at least one fluid extraction port.

6. The cartridge of claim 5, wherein the at least one fluid extraction port comprises a needleless injection port.

7. The cartridge of claim 1, wherein at least one of the plurality of valves comprises a pinch valve.

8. The cartridge of claim 1, wherein the central panel comprises a plurality of fluidic pathways.

9. The cartridge of claim 8, wherein the plurality of fluidic pathways of the central panel are fluidically connected to the plurality of fluidic pathways of each of the first and second end panels.

10. The cartridge of claim 8, wherein the central panel further comprises at least one pressure sensor configured to monitor fluid flow through the plurality of fluidic pathways of the central panel.

11. The cartridge of claim 8, wherein the plurality of fluidic pathways of the central panel are fluidically connected to one or more pumps.

12. The cartridge of claim 8, wherein the central panel is coupled to a vent manifold configured to provide sterile air to the plurality of fluidic pathways of the central panel.

13. The cartridge of claim 8, wherein the central panel is coupled to a degassing module comprising an air permeable membrane.

14. The cartridge of claim 1, wherein the central panel connects the first end panel and the second end panel via first and second bridges.

15. The cartridge of claim 1, wherein the fluidic manifold is fluidically connected to one or more modules of the cartridge.

16. The cartridge of claim 15, wherein the one or more modules of the cartridge are selected from the group consisting of an elutriation module, an electroporation module, a spinoculation module, and a cell sorting module.

17. The cartridge of claim 1, wherein the first end panel is fluidically connected to a first bioreactor module and the second end panel is fluidically connected to a second bioreactor module.

\* \* \* \* \*